US010894042B2

(12) United States Patent
Couvineau et al.

(10) Patent No.: US 10,894,042 B2
(45) Date of Patent: Jan. 19, 2021

(54) METHODS AND PHARMACEUTICAL COMPOSITIONS FOR THE TREATMENT OF CANCER

(71) Applicants: INSERM (INSTITUT NATIONAL DE LA SANTÉ ET DE LA RECHERCHE MÉDICALE), Paris (FR); UNIVERSITÉ PARIS DIDEROT—PARIS 7, Paris (FR)

(72) Inventors: Alain Couvineau, Paris (FR); Valérie Gratio, Paris (FR); Pascal Nicole, Paris (FR); Thierry Voisin, Paris (FR)

(73) Assignees: INSERM (INSTITUT NATIONAL DE LA SANTA ET DE LA RECHERCHE MEDICALE), Paris (FR); UNIVERSITE PARIS DIDEROT—PARIS 7, Paris (FR)

( * ) Notice: Subject to any disclaimer, the term of this patent is extended or adjusted under 35 U.S.C. 154(b) by 0 days.

(21) Appl. No.: 15/525,771

(22) PCT Filed: Nov. 10, 2015

(86) PCT No.: PCT/EP2015/076199
§ 371 (c)(1),
(2) Date: May 10, 2017

(87) PCT Pub. No.: WO2016/075134
PCT Pub. Date: May 19, 2016

(65) Prior Publication Data
US 2018/0296549 A1    Oct. 18, 2018

(30) Foreign Application Priority Data
Nov. 12, 2014  (EP) .................................... 14306798

(51) Int. Cl.
| *A61K 31/49* | (2006.01) |
| *A61K 31/47* | (2006.01) |
| *A61K 45/06* | (2006.01) |
| *A61K 31/435* | (2006.01) |
| *A61K 31/5513* | (2006.01) |
| *A61P 35/00* | (2006.01) |
| *A61K 31/472* | (2006.01) |
| *A61K 31/551* | (2006.01) |

(52) U.S. Cl.
CPC ............ *A61K 31/47* (2013.01); *A61K 31/435* (2013.01); *A61K 31/472* (2013.01); *A61K 31/551* (2013.01); *A61K 31/5513* (2013.01); *A61K 45/06* (2013.01); *A61P 35/00* (2018.01)

(58) Field of Classification Search
None
See application file for complete search history.

(56) References Cited

FOREIGN PATENT DOCUMENTS

| WO | 2000/047577 A1 | 8/2000 | |
| WO | WO-0047577 A1 * | 8/2000 | ........... C07D 215/46 |

OTHER PUBLICATIONS

Rouet-Benzineb et al (Orexins Acting at Native OX1 Receptor in Colon Cancer and Neuroblastoma Cells or at Recombinant OX1 Receptor Suppress Cell Growth by Inducing Apoptosis. The Journal of Biological Chemistry. vol. 279, No. 44, Issue of Oct. 29, 2004, pp. 45875-45886) (Year: 2004).*
Xu et al (Orexin receptors: Multi-functional therapeutic targets for sleeping disorders, eating disorders, drug addiction, cancers and other physiological disorders. Cellular Signalling. vol. 25, Issue 12, Dec. 2013, pp. 2413-2423) (Year: 2013).*
Venook (The Oncologist 2005;10:250-261). (Year: 2005).*
Tian-Rui et al: "Orexin receptors: Multi-functional therapeutic targets for sleeping disorders, eating disorders, drug addiction, cancers and other physiological disorders", Cellular Signalling, vol. 25, No. 12, pp. 2413-2423, Dec. 1, 2013.
M. Laburthe et al: "Orexins/hypocretins and orexin receptors in apoptosis: a mini-review" Acta Physiologica, vol. 198, No. 3, pp. 393-402, Mar. 1, 2010.

* cited by examiner

*Primary Examiner* — Jake M Vu
(74) *Attorney, Agent, or Firm* — W&C IP

(57) ABSTRACT

The present invention relates to methods and pharmaceutical compositions for the treatment of cancer. More particularly, the present invention relates to a method of treating cancer in subject in need thereof comprising administering the subject with a therapeutically effective amount of at least one OX1R antagonist.

11 Claims, 3 Drawing Sheets

METHODS AND PHARMACEUTICAL COMPOSITIONS FOR THE TREATMENT OF CANCER

FIELD OF THE INVENTION

Figure 1:
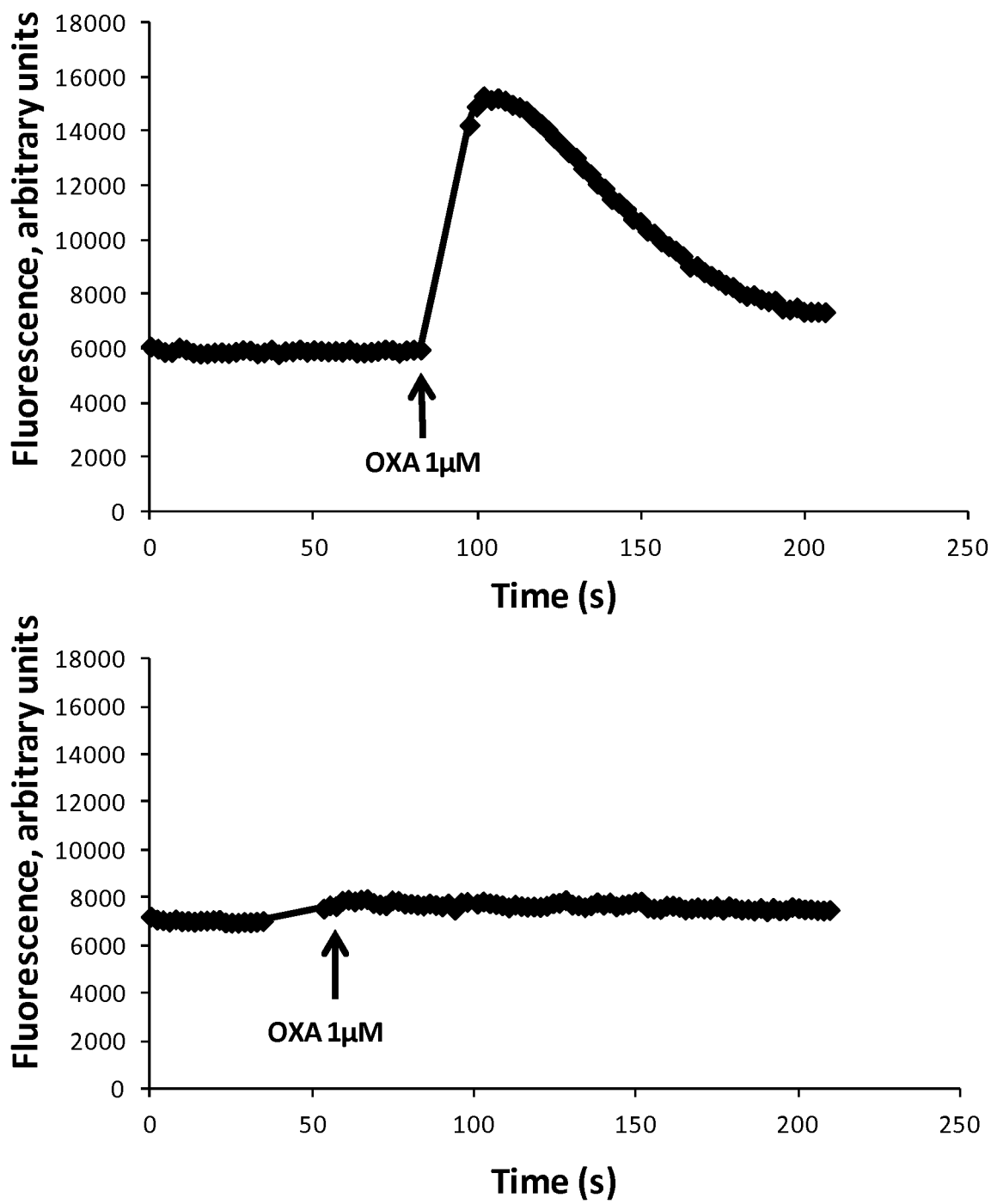

The present invention relates to methods and pharmaceutical compositions for the treatment of cancer.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour. Orexins regulate states of sleep and wakefulness opening potentially novel therapeutic approaches for narcoleptic or insomniac patients. Orexins have also been indicated as playing a role in arousal, reward, learning and memory. Two orexin receptors have been cloned and characterized in mammals. They belong to the super family of G-protein coupled receptors (7-transmembrane spanning receptor) (Sakurai T. et al., Cell, 1998, 92, 573-585): the orexin-1 receptor (OX1R or HCTR1) is more selective for OX-A than OX-B and the orexin-2 receptor (OX2R or HCTR2) binds OX-A as well as OX-B. A recent study shows that activation of OX1R by orexin can promote robust in vitro and in vivo apoptosis in colon cancer cells even when they are resistant to the most commonly used drug in colon cancer chemotherapy (Voisin T, El Firar A, Fasseu M, Rouyer-Fessard C, Descatoire V, Walker F, Paradis V, Bedossa P, Henin D, Lehy T, Laburthe M. Aberrant expression of OX1 receptors for orexins in colon cancers and liver metastases: an openable gate to apoptosis. Cancer Res. 2011 May 1; 71(9):3341-51). In particular, it was shown that OX1R promotes apoptosis in the cancer cell lines through a mechanism which is not related to Gq-mediated phopholipase C activation and cellular calcium transients. Orexins induce indeed tyrosine phosphorylation of 2 tyrosine-based motifs in OX1R, ITIM and ITSM, resulting in the recruitment of the phosphotyrosine phosphatase SHP-2, the activation of which is responsible for mitochondrial apoptosis (Voisin T, El Firar A, Rouyer-Fessard C, Gratio V, Laburthe M. A hallmark of immunoreceptor, the tyrosine-based inhibitory motif ITIM, is present in the G protein-coupled receptor OX1R for orexins and drives apoptosis: a novel mechanism. FASEB J. 2008 June; 22(6):1993-2002; El Firar A, Voisin T, Rouyer-Fessard C, Ostuni M A, Couvineau A, Laburthe M. Discovery of a functional immunoreceptor tyrosine-based switch motif in a 7-transmembrane-spanning receptor: role in the orexin receptor OX1R-driven apoptosis. FASEB J. 2009 December; 23(12):4069-80. doi: 10.1096/fj.09-131367. Epub 2009 Aug. 6.). Remarkably, all primary colorectal tumors regardless of their localization and Duke's stages expressed OX1R while adjacent normal colonocytes as well as control normal tissues were negative. Besides, expression of OX1R has been recently confirmed in pancreatic cancer, hepatocarcimomas, and advanced prostate cancer. Accordingly the prior art supports that OX1R is an Achilles's heel of cancers (even chemoresistance) and suggests that OX1R is a relevant target for cancer therapy.

SUMMARY OF THE INVENTION

The present invention relates to methods and pharmaceutical compositions for the treatment of cancer. In particular, the present invention is defined by the claims.

DETAILED DESCRIPTION OF THE INVENTION

The prior art teaches that orexin (i.e. the natural OX1R agonist) are suitable for triggering apoptosis in cancer cells. Surprisingly, the inventors demonstrate that the antagonists of the prior art (as defined hereinafter) are also able to trigger apoptosis in pancreatic and colorectal cancer cell lines.

Accordingly, the present invention relates to a method for triggering apoptosis in a population of cancer cells comprising contacting the population of cancer cells with an amount of at least one OX1R antagonist. More particularly, the present invention relates to a method of treating cancer in subject in need thereof comprising administering the subject with a therapeutically effective amount of at least one OX1R antagonist.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

Typically, the cancer may be selected from the group consisting of bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyo sarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In some embodiments, the subject suffers from an epithelial cancer. As used herein, the term "epithelial cancer" refers to any malignant process that has an epithelial origin. Examples of epithelial cancers include, but are not limited to, a gynecological cancer such as endometrial cancer, ovarian cancer, cervical cancer, vulvar cancer, uterine cancer or fallopian tube cancer, breast cancer, prostate cancer, lung cancer, pancreatic cancer, urinary cancer, bladder cancer, head and neck cancer, oral cancer and liver cancer. An epithelial cancer may be at different stages as well as varying degrees of grading. In some embodiments, the epithelial cancer is selected from the group consisting of breast cancer, prostate cancer, lung cancer, pancreatic cancer, bladder cancer and ovarian cancer. In some embodiments, the epithelial cancer is a liver cancer, in particular a hepatocellular carcinoma. In some embodiments, the epithelial cancer is breast cancer. In some embodiments, the epithelial cancer is ovarian cancer. In some embodiments, the epithelial cancer is prostate cancer, in particular advanced prostate cancer. In some embodiments, the epithelial cancer is lung cancer. In some embodiments, the epithelial cancer is head and neck cancer. In some embodiments, the epithelial cancer is head and neck squamous cell carcinoma.

As used herein the term "pancreatic cancer" or "pancreas cancer" as used herein relates to cancer which is derived from pancreatic cells. In particular, pancreatic cancer included pancreatic adenocarcinoma (e.g., pancreatic ductal adenocarcinoma) as well as other tumors of the exocrine pancreas (e.g., serous cystadenomas), acinar cell cancers, intraductal papillary mucinous neoplasms (IPMN) and pancreatic neuroendocrine tumors (such as insulinomas).

As used herein the term "hepatocellular carcinoma" has its general meaning in the art and refers to the cancer developed in hepatocytes. In general, liver cancer indicates hepatocellular carcinoma in large. HCC may be caused by an infectious agent such as hepatitis B virus (HBV, hereinafter may be referred to as HBV) or hepatitis C virus (HCV, hereinafter may be referred to as HCV). In some embodiments, HCC results from alcoholic steatohepatitis or non-alcoholic steatohepatitis (hereinafter may be abbreviated to as "NASH"). In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC.

As used herein the term "advanced prostate cancer" has its general meaning in the art. "Castration resistant prostate cancer," "CaP," "androgen-receptor dependent prostate cancer," "androgen-independent prostate cancer," are used interchangeably to refer to prostate cancer in which prostate cancer cells "grow" {i.e., increase in number) in the absence of androgens and/or in the absence of expression of androgen receptors on the cancer cells.

As used herein, the term "OX1R" has its general meaning in the art and refers to the 7-transmembrane spanning receptor OX1R for orexins.

As used herein the term "OX1R antagonist" has its general meaning in the art and refers to any compound that is able to inhibit the calcium-dependent signalling pathway induced by Orexin. It is known that binding of the orexin to its receptor triggers an influx of calcium, which is coupled to activation of Erk. The receptors also couple to a phospholipase C (PLC)-mediated pathway that releases intracellular calcium stores. The utility of the compounds in accordance with the present invention as orexin receptor OX1R antagonists may be readily determined without undue experimentation by methodology well known in the art, including the "FLIPR Ca2+ Flux Assay" (Okumura et al, Biochem. Biophys. Res. Comm. 280:976-981, 2001). In a typical experiment the OX1 receptor antagonistic activity of the compounds of the present invention was determined in accordance with the following experimental method. For intracellular calcium measurements, Chinese hamster ovary (CHO) cells expressing the rat orexin-1 receptor are grown in Iscove's modified DMEM containing 2 mM L-glutamine, 0.5 g/ml G418, 1% hypoxanthine-thymidine supplement, 100 U/ml penicillin, 100 ug/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% CO2. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 ul assay buffer and then incubated for 60 min (37° C., 5% CO2) in 60 ul assay buffer containing 1 uM Fluo-4AM ester, 0.02% pluronic acid, and 1% BSA. The dye loading solution is then aspirated and cells are washed 3 times with 100 ul assay buffer. 30 ul of that same buffer is left in each well. Within the Fluorescent Imaging Plate Reader (FLIPR, Molecular Devices), test compounds are added to the plate in a volume of 25 ul, incubated for 5 min and finally 25 ul of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. Alternatively, compound potency can be assessed by a radioligand binding assay (described in Bergman et. al. Bioorg. Med. Chem. Lett. 2008, 18, 1425-1430) in which the inhibition constant is determined in membranes prepared from CHO cells expressing the OX1 receptor. The intrinsic orexin receptor antagonist activity of a compound which may be used in the present invention may be determined by these assays.

OX1R antagonists are well known to the skilled person who may easily identify such antagonists from the following literature:

Boss C, Roch-Brisbare C, Steiner M A, Treiber A, Dietrich H, Jenck F, von Raumer M, Sifferlen T, Brotschi C, Heidmann B, Williams J T, Aissaoui H, Siegrist R, Gatfield J. Structure-Activity Relationship, Biological, and Pharmacological Characterization of the Proline Sulfonamide ACT-462206: a Potent, Brain-Penetrant Dual Orexin1/Orexin2 Receptor Antagonist. ChemMedChem. 2014 Aug. 21.

Christopher J A. Orexin receptor antagonists. Pharm Pat Anal. 2012 July; 1(3):329-46.

Coleman P J, Schreier J D, Cox C D, Breslin M J, Whitman D B, Bogusky M J, McGaughey G B, Bednar R A, Lemaire W, Doran S M, Fox S V, Garson S L, Gotter A L, Harrell C M, Reiss D R, Cabalu T D, Cui D, Prueksaritanont T, Stevens J, Tannenbaum P L, Ball R G, Stellabott J, Young S D, Hartman G D, Winrow C J, Renger J J. Discovery of [(2R,5R)-5-{[(5-fluoropyridin-2-yl)oxy]methyl}-2-methylpiperidin-1-yl][5-methyl-2-(pyrimidin-2-yl)phenyl]methanone (MK-6096): a dual orexin receptor antagonist with potent sleep-promoting properties. ChemMedChem. 2012 Mar. 5; 7(3):415-24, 337.

Cox C D, Breslin M J, Whitman D B, Schreier J D, McGaughey G B, Bogusky M J, Roecker A J, Mercer S P, Bednar R A, Lemaire W, Bruno J G, Reiss D R, Harrell C M, Murphy K L, Garson S L, Doran S M, Prueksaritanont T, Anderson W B, Tang C, Roller S, Cabalu T D, Cui D, Hartman G D, Young S D, Koblan K S, Winrow C J, Renger J J, Coleman P J. Discovery of the dual orexin receptor antagonist [(7R)-4-(5-chloro-1,3-benzoxazol-2-yl)-7-methyl-1,4-diazepan-1-yl][5-methyl-2-(2H-1,2,3-triazol-2-yl)phenyl]methanone (MK-4305) for the treatment of insomnia. J Med Chem. 2010 Jul. 22; 53(14):5320-32.

Jiaqiang Cai, Fiona E Cooke, Bradley S Sherborne Antagonists of the orexin receptors Expert Opinion on Therapeutic Patents May 2006, Vol. 16, No. 5, Pages 631-646: 631-646.

John A Christopher, Miles S Congreve Treatment and prevention of various therapeutic conditions using OX receptor antagonistic activity (WO2012081692) Expert Opinion on Therapeutic Patents February 2013, Vol. 23, No. 2, Pages 273-277: 273-277.

Langmead C J, Jerman J C, Brough S J, Scott C, Porter R A, Herdon H J. Characterisation of the binding of [3H]—SB-674042, a novel nonpeptide antagonist, to the human orexin-1 receptor. Br J Pharmacol. 2004 January; 141(2):340-6. Epub 2003 Dec. 22.

Paul J Coleman, John J Renger Orexin receptor antagonists: a review of promising compounds patented since 2006 Expert Opinion on Therapeutic Patents March 2010, Vol. 20, No. 3, Pages 307-324: 307-324.

Perrey D A, German N A, Gilmour B P, Li J X, Harris D L, Thomas B F, Zhang Y. Substituted tetrahydroisoquinolines as selective antagonists for the orexin 1 receptor. J Med Chem. 2013 Sep. 12; 56(17):6901-16.

Perrey D A, Gilmour B P, Runyon S P, Thomas B F, Zhang Y. Diaryl urea analogues of SB-334867 as orexin-1 receptor antagonists. Bioorg Med Chem Lett. 2011 May 15; 21(10):2980-5.

Porter R A, Chan W N, Coulton S, Johns A, Hadley M S, Widdowson K, Jerman J C, Brough S J, Coldwell M, Smart D, Jewitt F, Jeffrey P, Austin N. 1,3-Biarylureas as selective non-peptide antagonists of the orexin-1 receptor. Bioorg Med Chem Lett. 2001 Jul. 23; 11(14): 1907-10.

Roecker A J, Coleman P J (2008). "Orexin receptor antagonists: medicinal chemistry and therapeutic potential". Curr Top Med Chem 8 (11): 977-87.

Roecker A J, Coleman P J. Orexin receptor antagonists: medicinal chemistry and therapeutic potential. Curr Top Med Chem. 2008; 8(11):977-87.

Roecker A J, Mercer S P, Harrell C M, Garson S L, Fox S V, Gotter A L, Prueksaritanont T, Cabalu T D, Cui D, Lemaire W, Winrow C J, Renger J J, Coleman P J. Discovery of dual orexin receptor antagonists with rat sleep efficacy enabled by expansion of the acetonitrile-assisted/diphosgene-mediated 2,4-dichloropyrimidine synthesis. Bioorg Med Chem Lett. 2014 May 1; 24(9): 2079-85.

Smart D, Sabido-David C, Brough S J, Jewitt F, Johns A, Porter R A, Jerman J C. SB-334867-A: the first selective orexin-1 receptor antagonist. Br J Pharmacol. 2001 March; 132(6):1179-82.

Whitman D B, Cox C D, Breslin M J, Brashear K M, Schreier J D, Bogusky M J, Bednar R A, Lemaire W, Bruno J G, Hartman G D, Reiss D R, Harrell C M, Kraus R L, Li Y, Garson S L, Doran S M, Prueksaritanont T, Li C, Winrow C J, Koblan K S, Renger J J, Coleman P J. Discovery of a potent, CNS-penetrant orexin receptor antagonist based on an n,n-disubstituted-1,4-diazepane scaffold that promotes sleep in rats. ChemMedChem. 2009 July; 4(7):1069-74.

Yoshida Y, Terauchi T, Naoe Y, Kazuta Y, Ozaki F, Beuckmann C T, Nakagawa M, Suzuki M, Kushida I, Takenaka O, Ueno T, Yonaga M. Design, synthesis, and structure-activity relationships of a series of novel N-aryl-2-phenylcyclopropanecarboxamide that are potent and orally active orexin receptor antagonists. Bioorg Med Chem. 2014 Sep. 8. pii: S0968-0896(14) 00630-0.

Other examples of OX1R antagonists are also described in the following patent publications:
EP0849361
US20080132490
US20090163485
U.S. Pat. No. 6,309,854
WO 2014099698
WO00047576
WO00047577
WO00047580
WO01000787
WO01068609
WO01085693
WO01096302
WO02044172
WO02051232
WO02051838
WO02089800

WO02090355
WO03002559
WO03002561
WO03032991
WO03037847
WO03041711
WO03051368
WO03051871
WO03051872
WO03051873
WO19909024
WO19958533
WO2003002561
WO2003051872
WO2004004733
WO2004026866
WO2004033418
WO2004041791
WO2004041807
WO2004041816
WO2004052876
WO2004085403
WO2004096780
WO2005060959
WO2005075458
WO2005118548
WO2006067224
WO2006110626
WO2006127550
WO2007019234
WO2007025069
WO2007061763
WO2007085718
WO2007122591
WO2007126934
WO2007126935
WO2008008517
WO2008008518
WO2008008551
WO2008020405
WO2008026149
WO2008038251
WO2008065626
WO2008078291
WO2008081399
WO2008107335
WO2008110488
WO2008117241
WO2008143856
WO2008147518
WO2008150364
WO2009003993
WO2009003997
WO2009004585
WO2009011775
WO2009016087
WO2009016564
WO2009020642
WO2009022311
WO2009034133
WO2009058238
WO2009079637
WO2011053522
WO2013059163
WO2013059222
WO2013062857
WO2013062858
WO2014066196
WO2014085208
WO2014099696
and WO2014099697.

In some embodiments, the OX1R antagonist of the present invention is SB408124 which is:

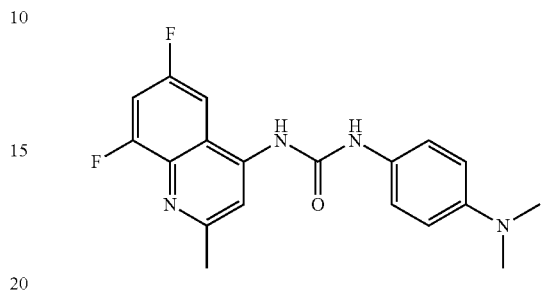

In some embodiments, the OX1R antagonist of the present invention is selected from the group consisting of:

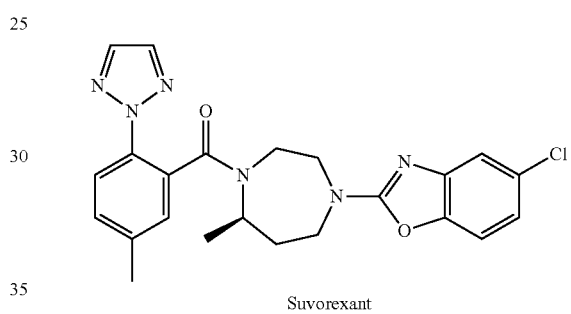

Suvorexant

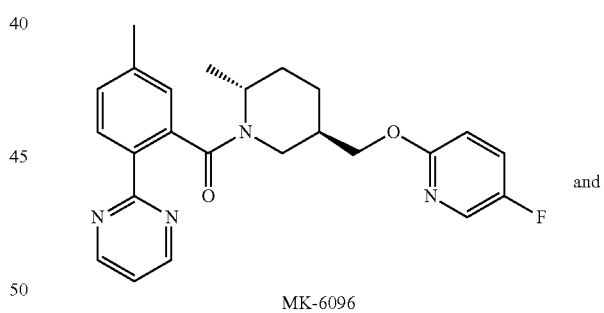

MK-6096

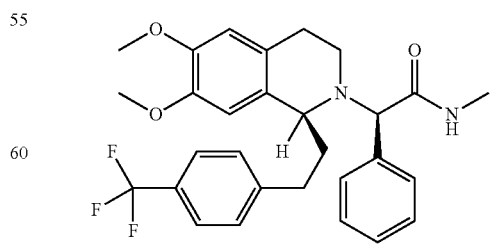

In some embodiments, the OX1R antagonist of the present invention is selected from the group consisting of:

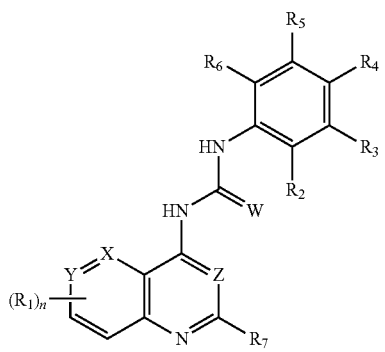
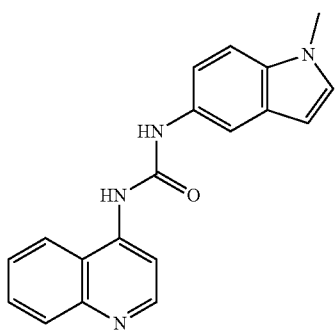
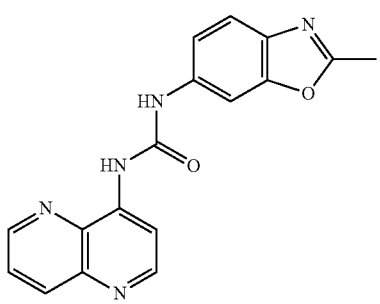
SB-334867-A
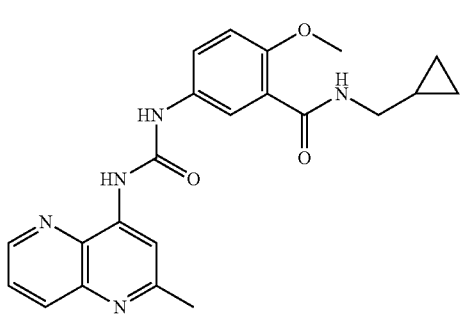
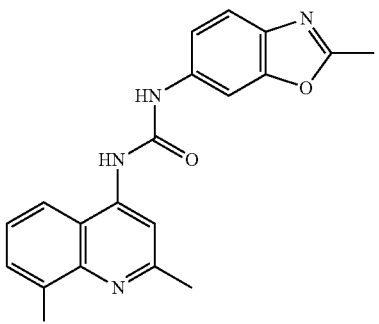
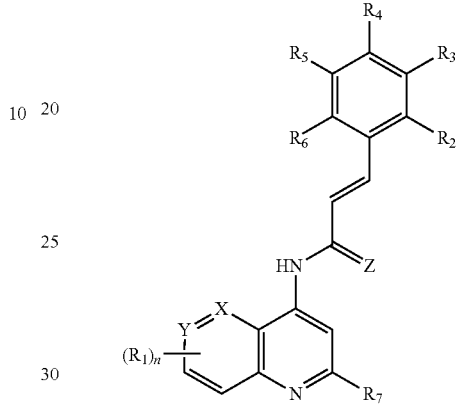
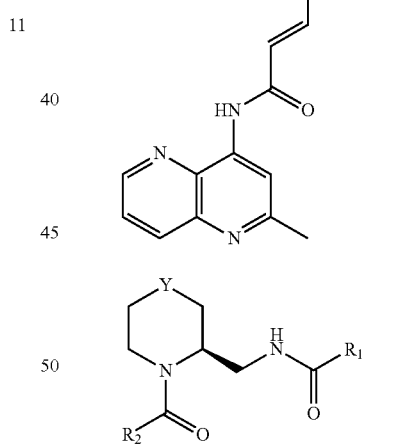
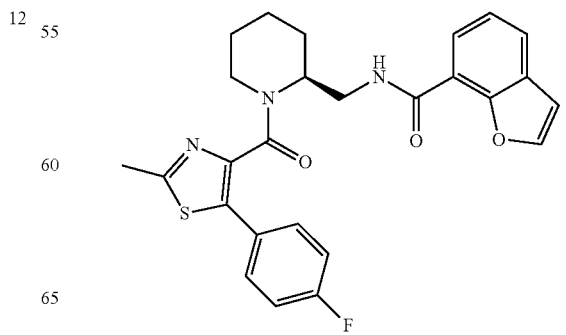

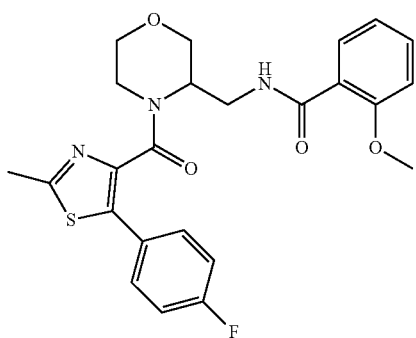
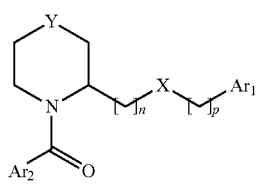
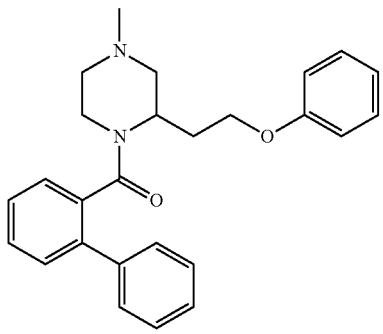
21 Y = O
22 Y = CH₂
23 Y = Bond
24
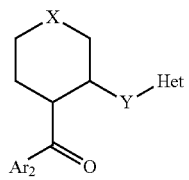
25
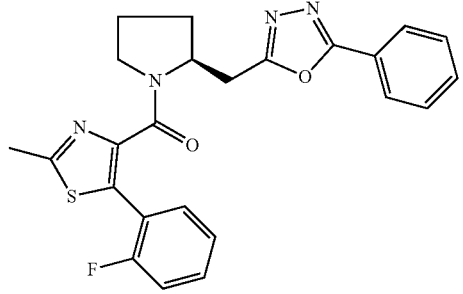
SB-674042
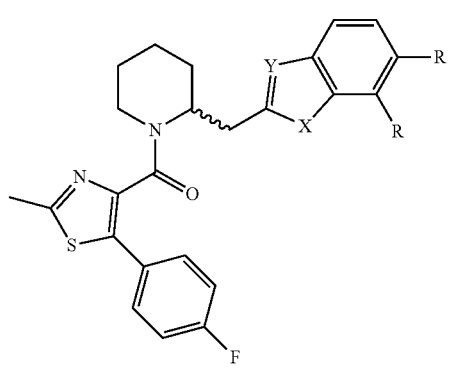
27 X = O, Y = CH, R = H
28 X = S, Y = CH, R = H
29 X = NH, Y = CH, R = H
30 X = NH, Y = N, R = F
31
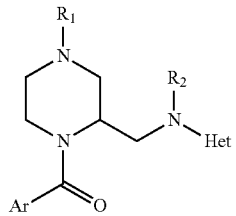
32
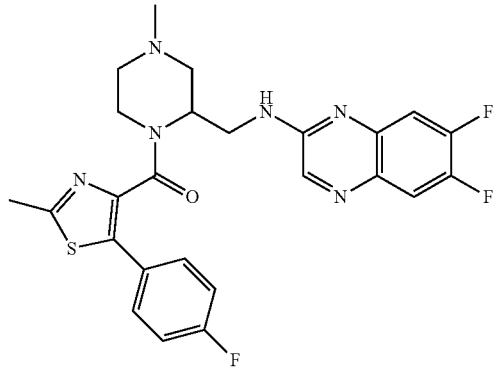

33 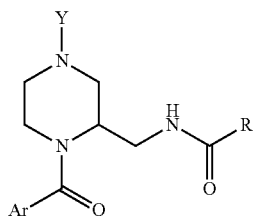
34 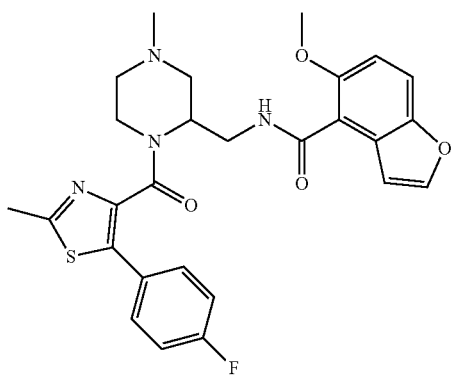
35 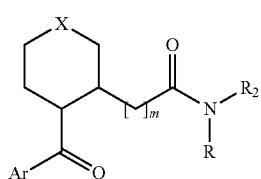
36 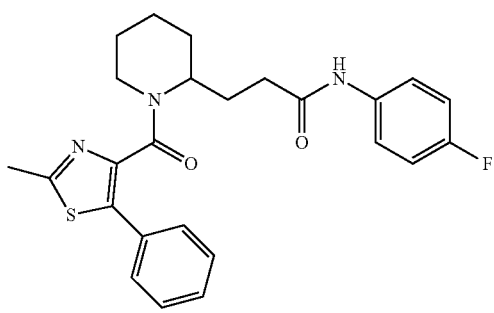
37 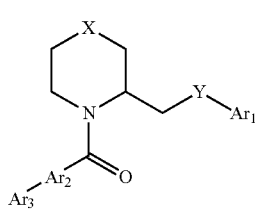
38 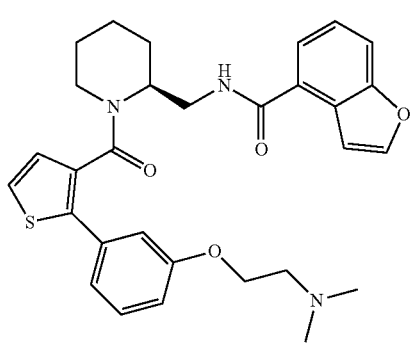
39 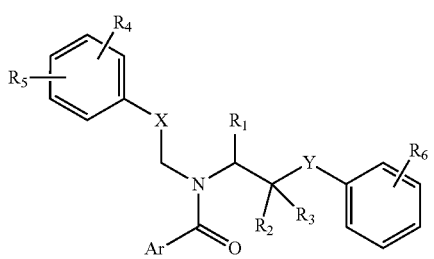
40 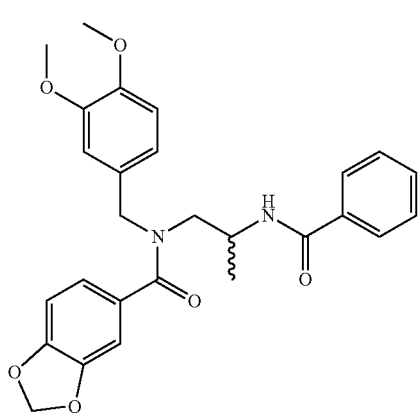
41 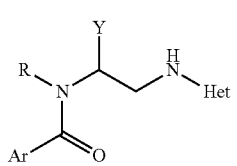
42 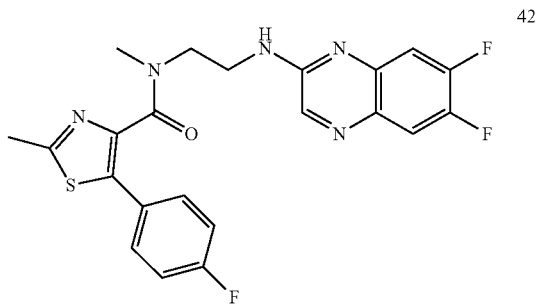
43 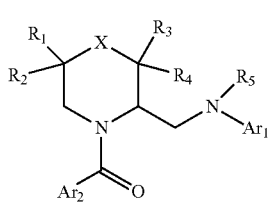

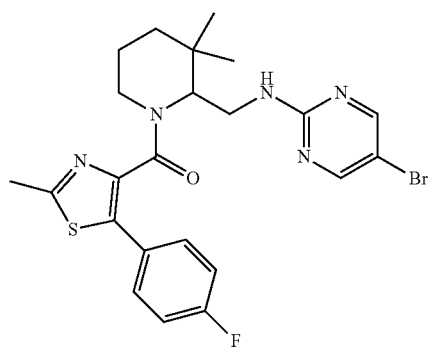
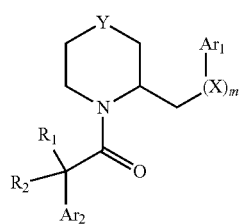
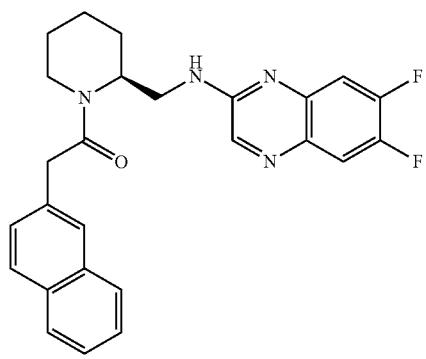
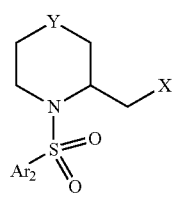
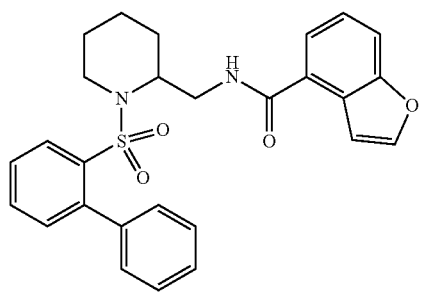
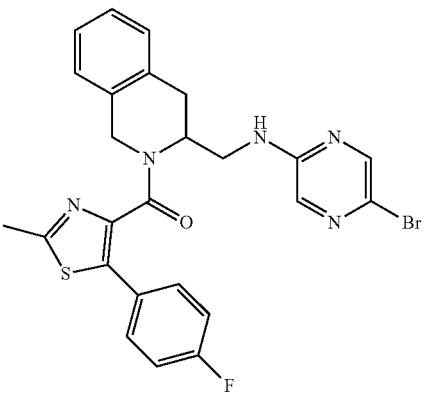
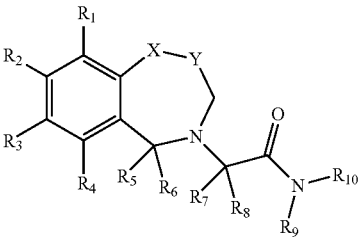
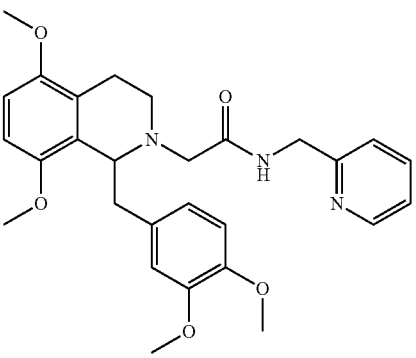
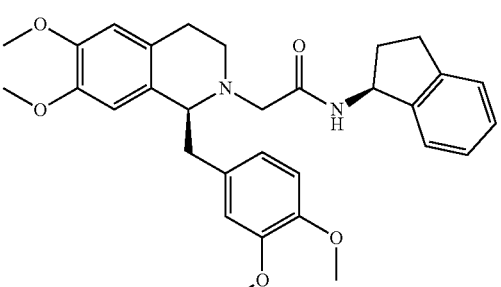
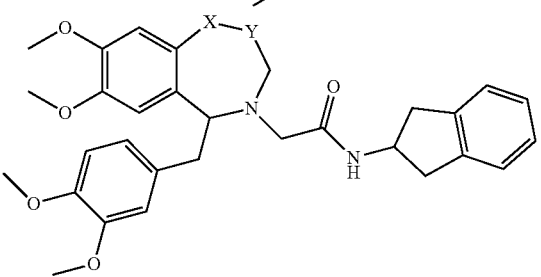
53 X = Y = CH$_2$
54 X = SO$_2$, Y = CH$_2$ 55
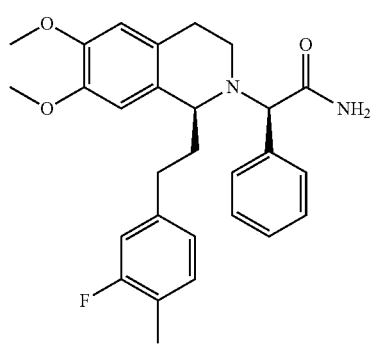
56
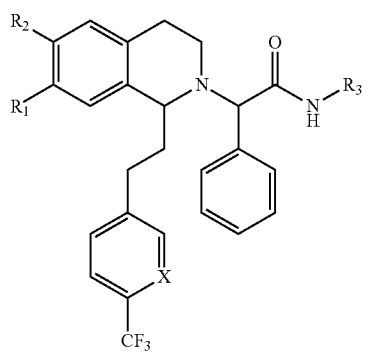
57
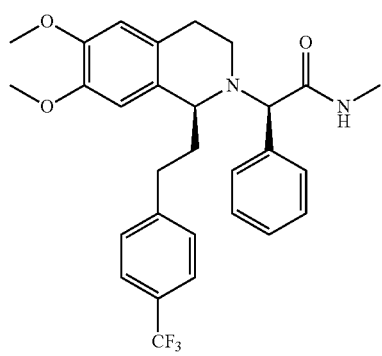
58
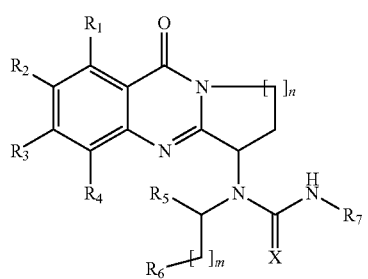
59
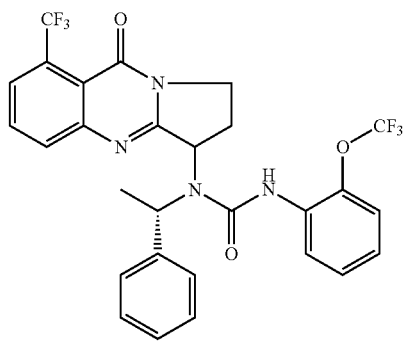
60
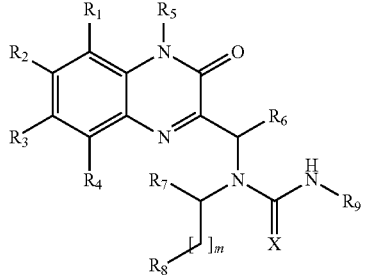
61
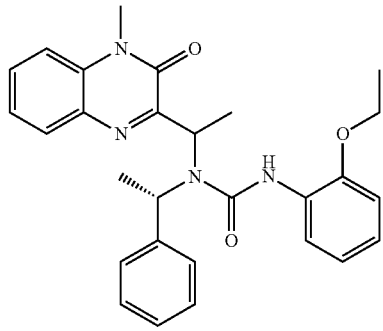
62
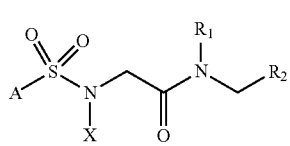
63
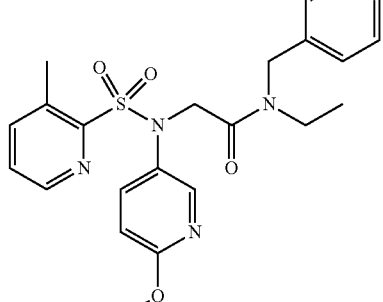
64
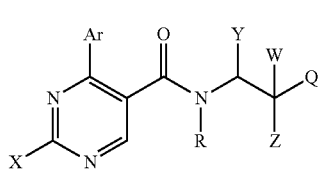

65
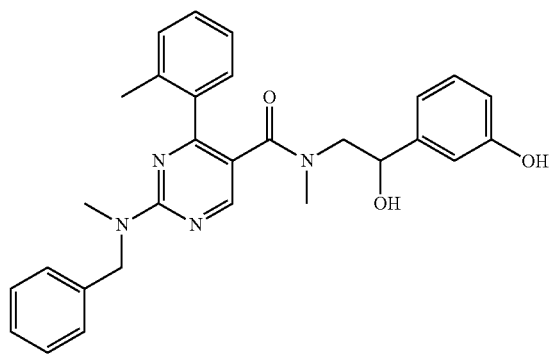
66
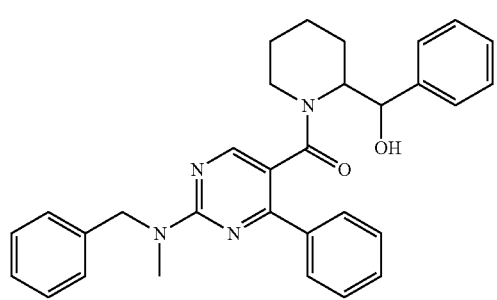
64
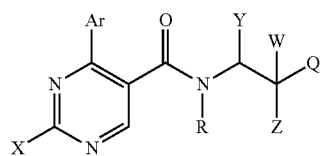
65
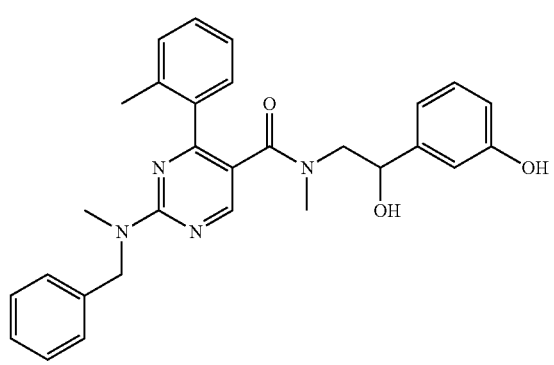
66
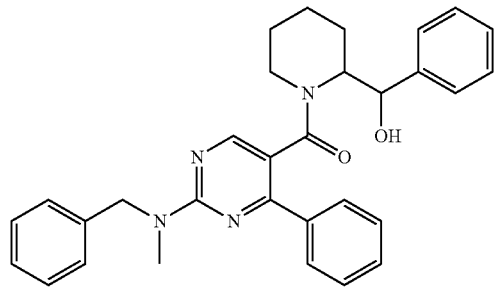
67
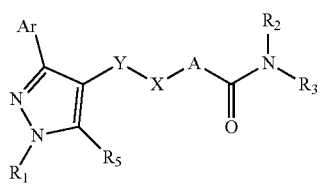
68
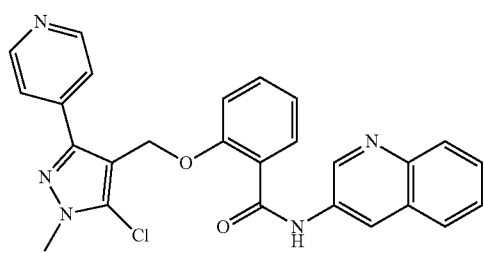
69
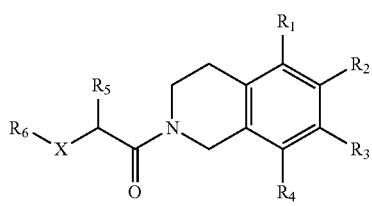
70
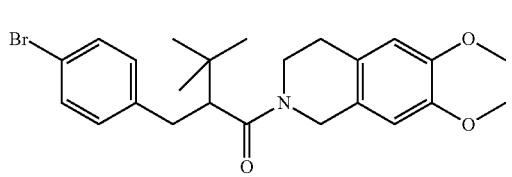
71
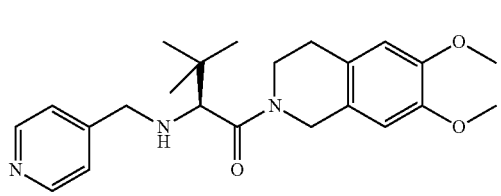
72
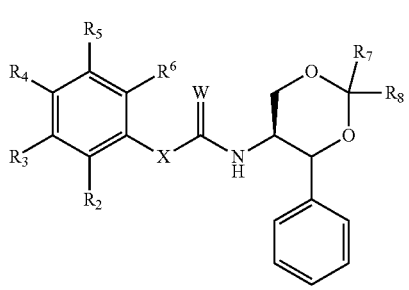

-continued
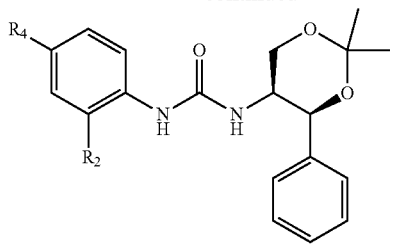
73 R₂ = Cl, R₄ = Br, p$K_b$ = 7.6
74 R₂ = Br, R₄ = Br, p$K_b$ = 8.3
75 R₂ = Cl, R₄ = Cl, p$K_b$ = 7.6
76 R₂ = Br, R₄ = CH₃, p$K_b$ = 8.2
In some embodiments, the OX1R antagonist of the present invention is selected from the group consisting of:
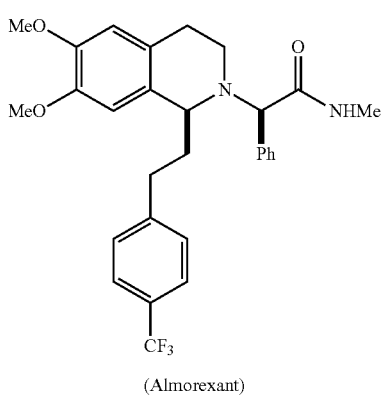
(Almorexant)
1
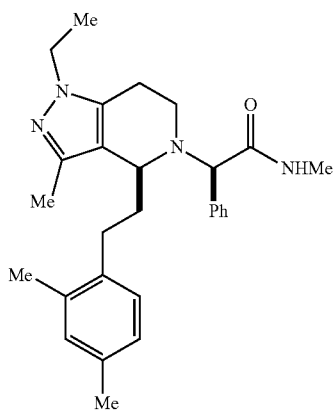
2
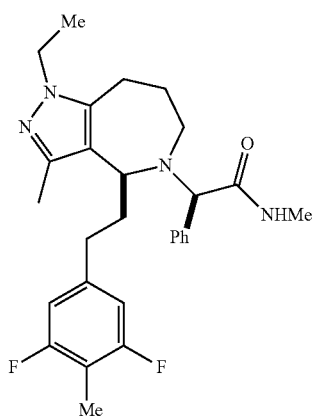
3
-continued
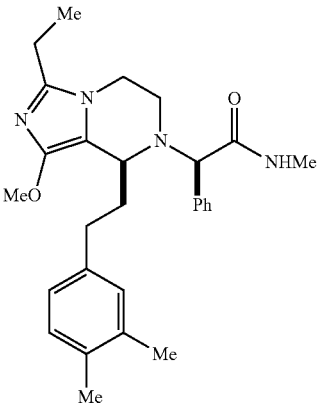
4
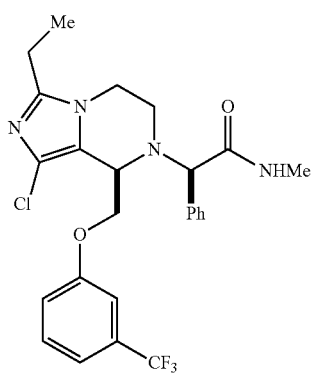
5
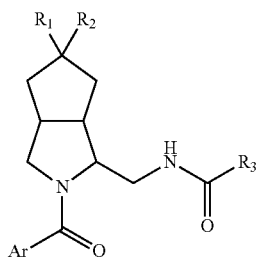
6
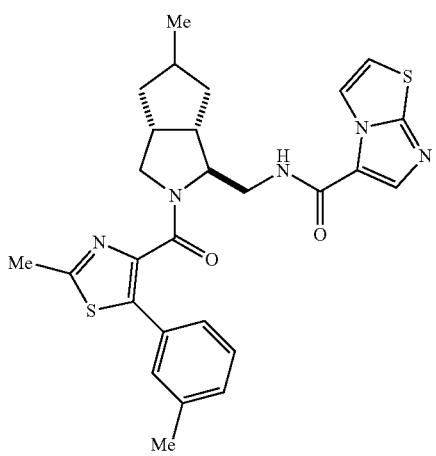
7

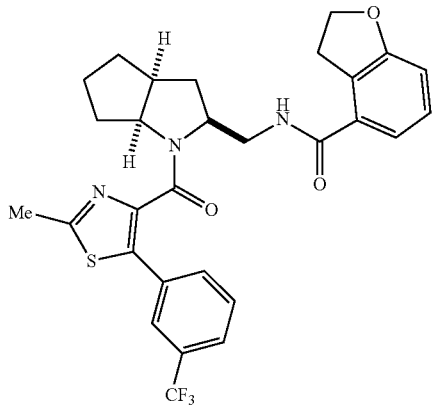
8
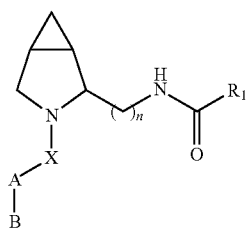
9
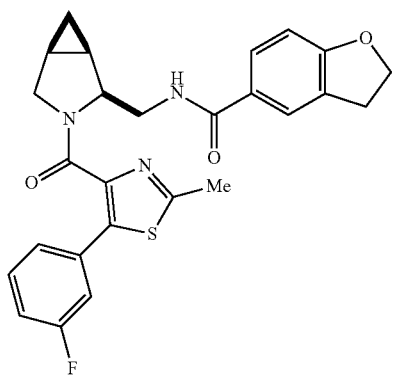
10
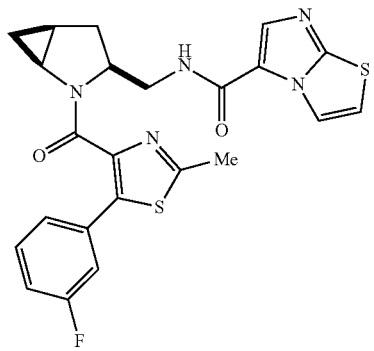
11
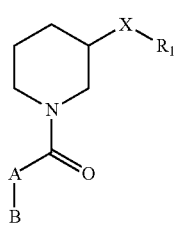
12
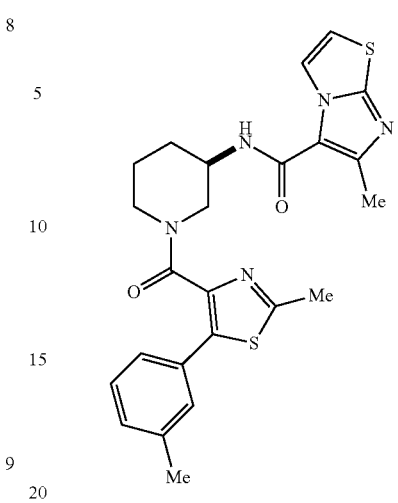
13
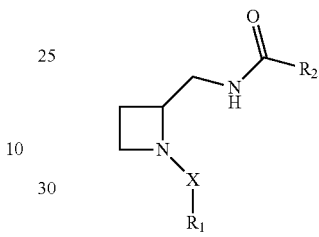
14
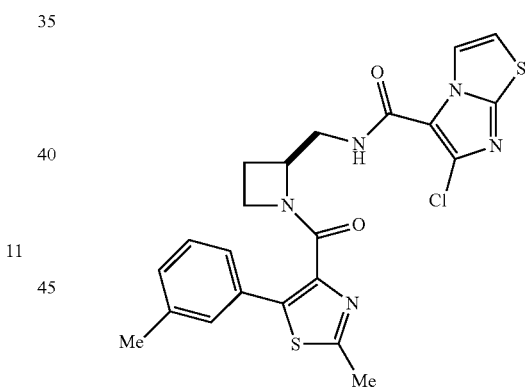
15
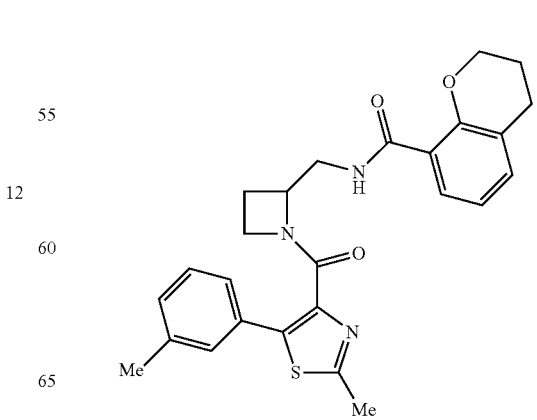
16

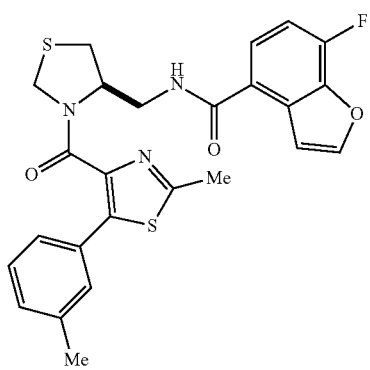
17
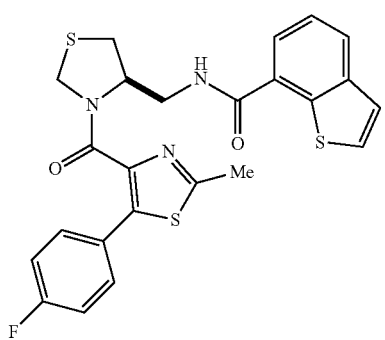
18
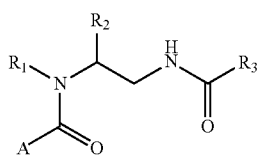
19
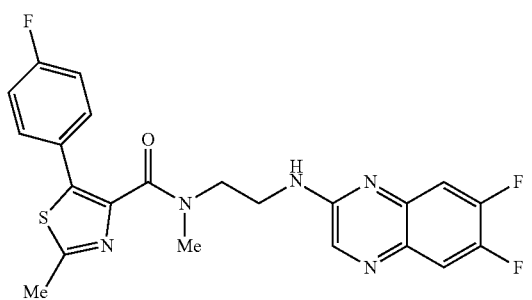
20
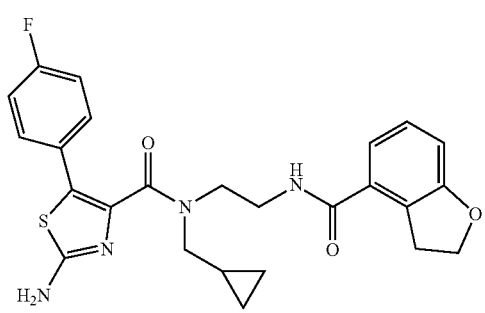
21
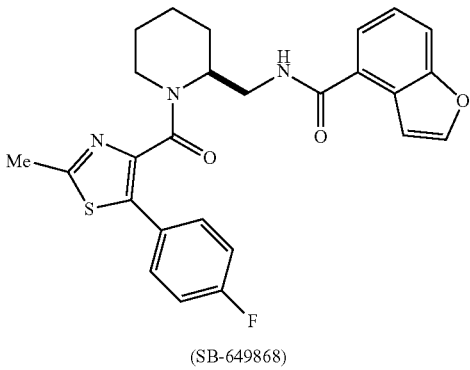
22
(SB-649868)
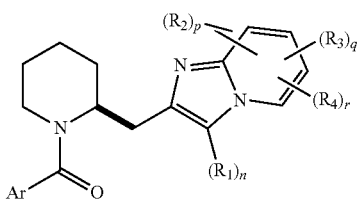
23
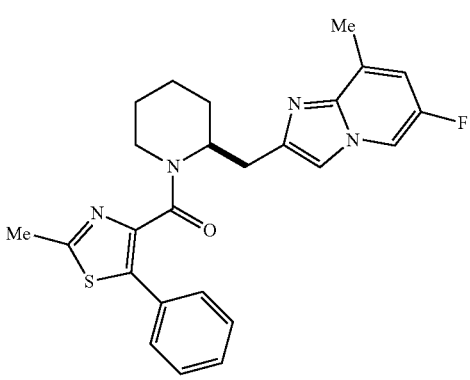
24
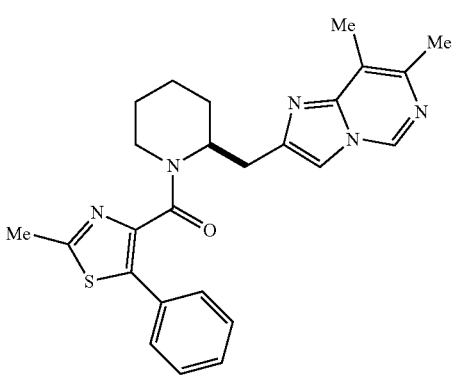
25
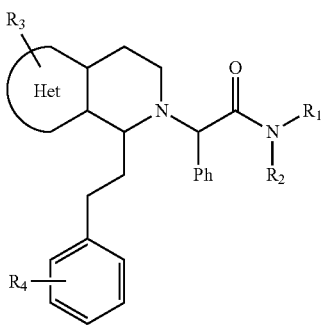
26

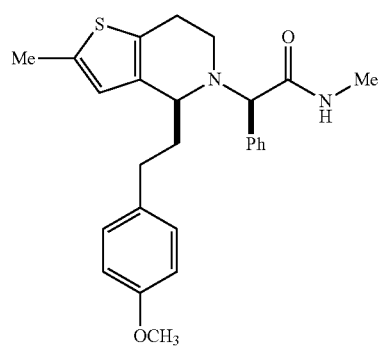
27
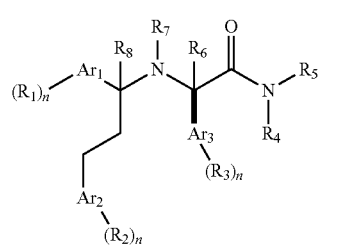
28
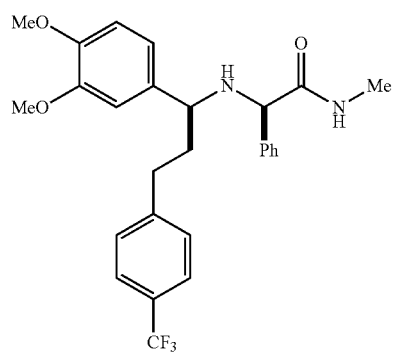
29
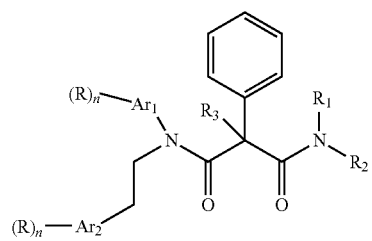
30
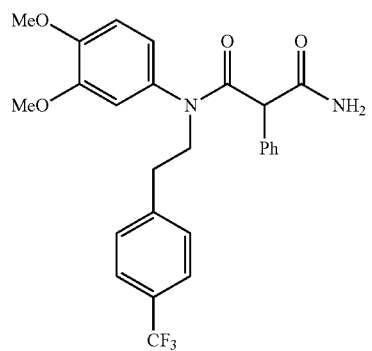
31
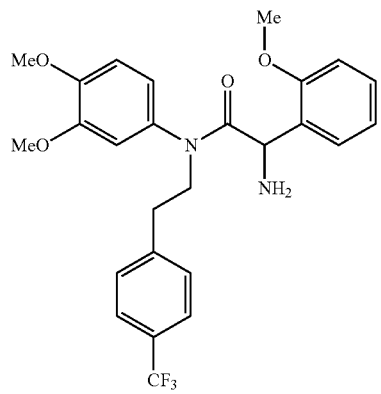
32
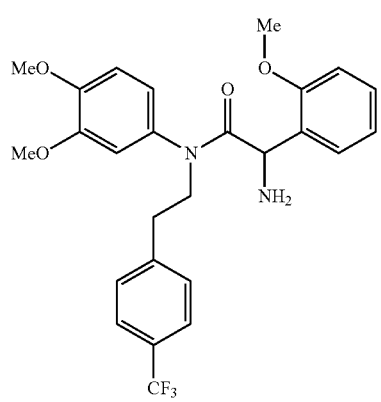
33
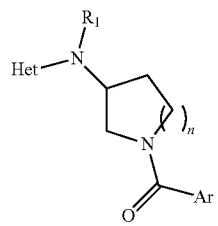
34
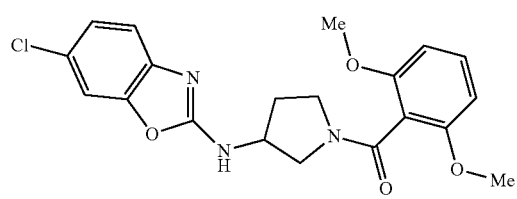
35
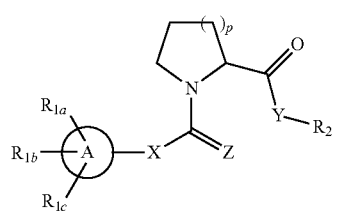
36

37
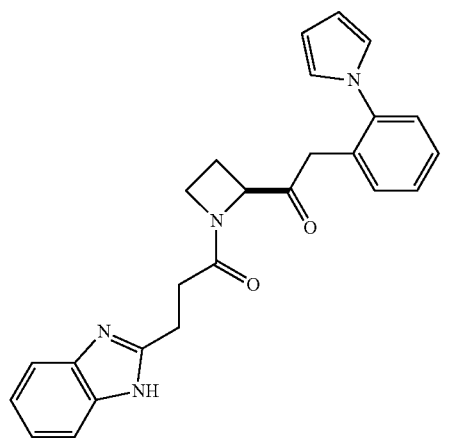
38
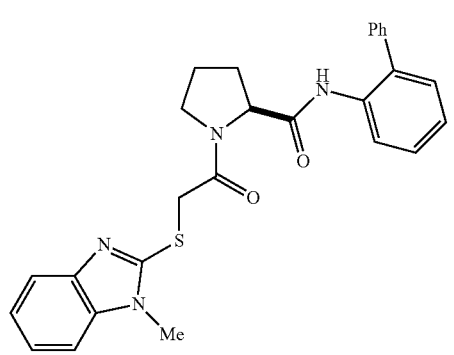
39
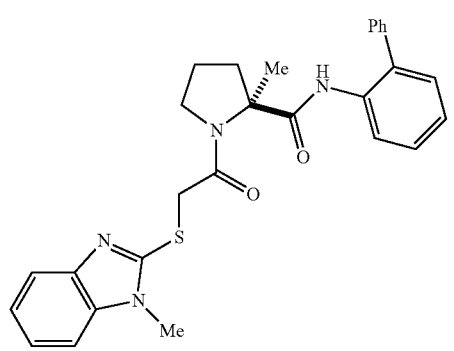
40
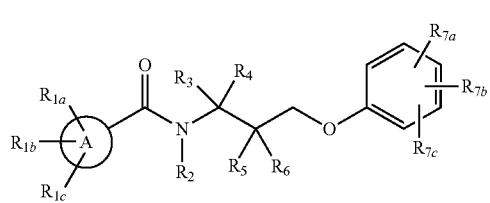
41
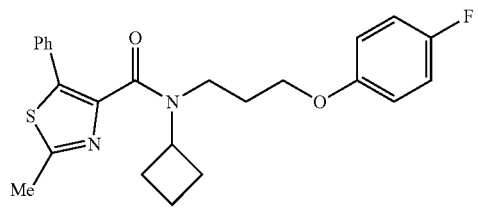
42
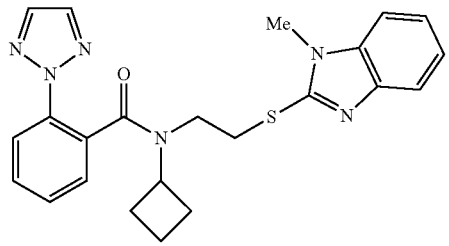
43
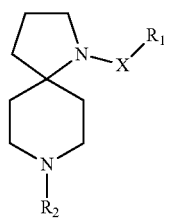
44
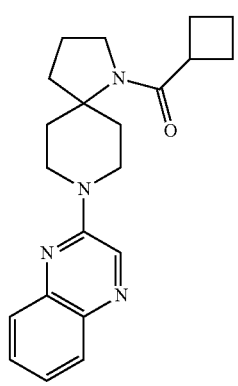
45
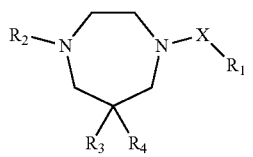
46
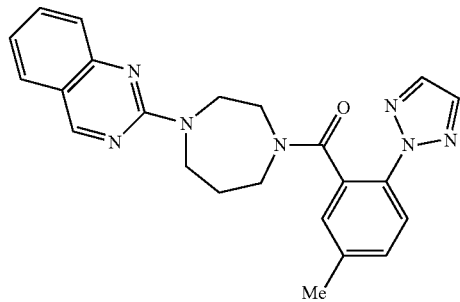
47
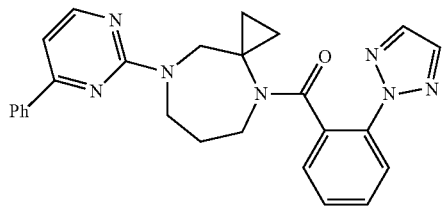

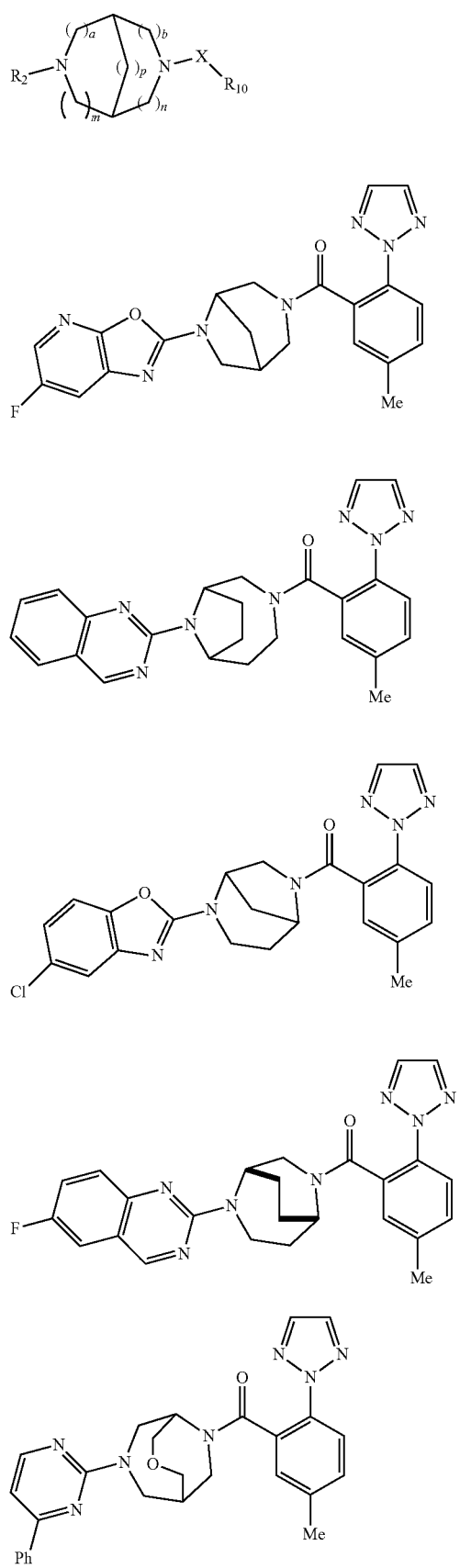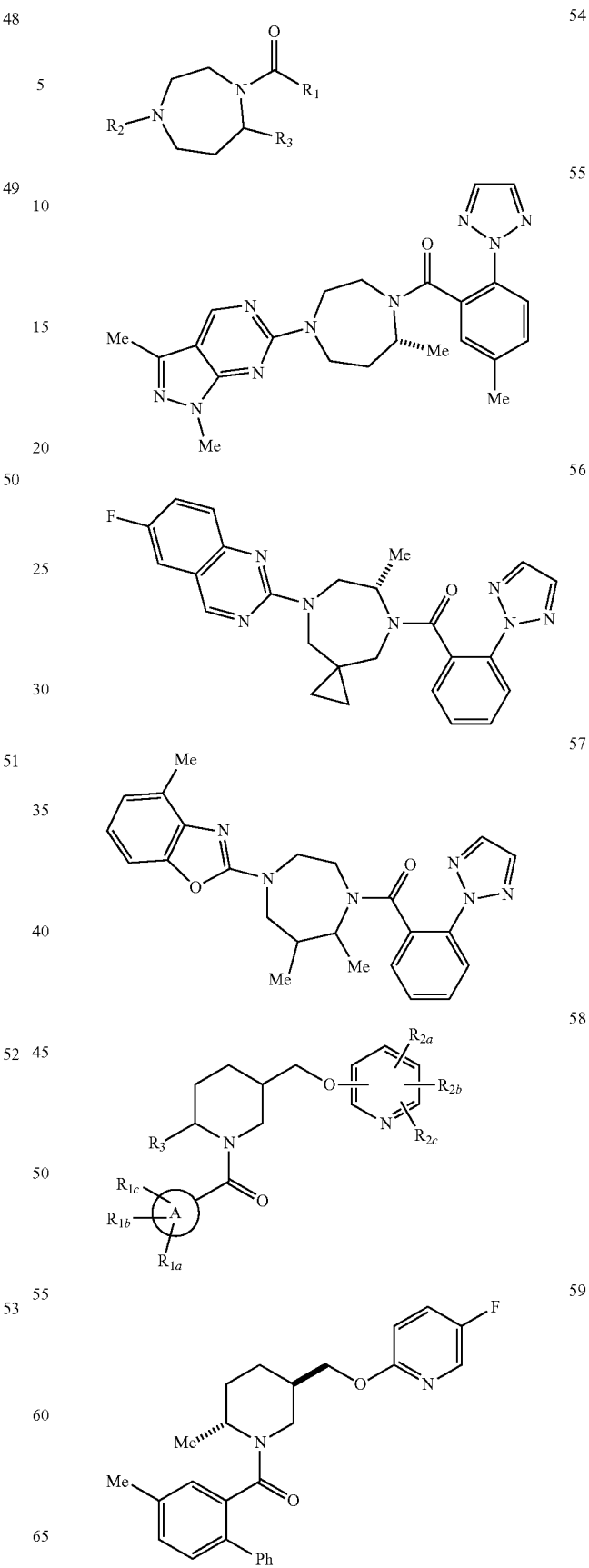

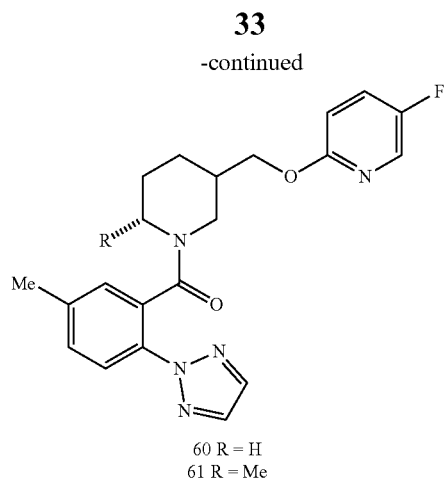
60 R = H
61 R = Me
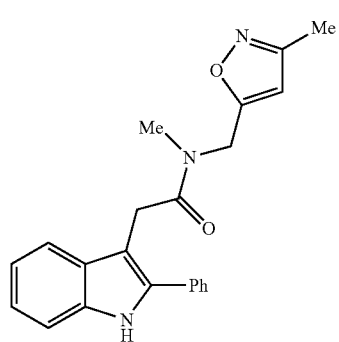
62
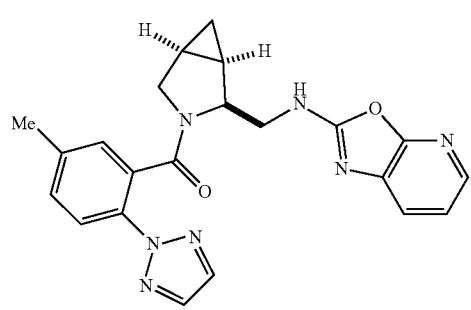
63
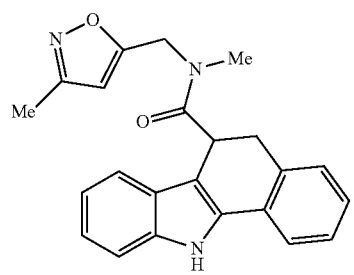
64
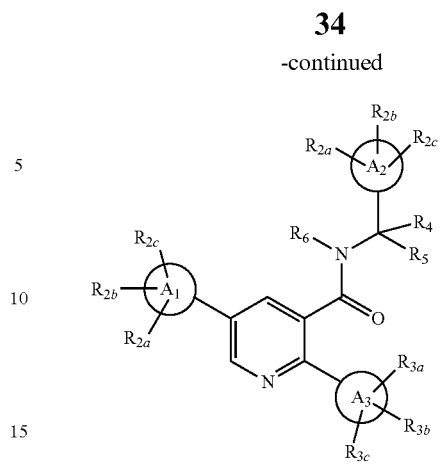
65
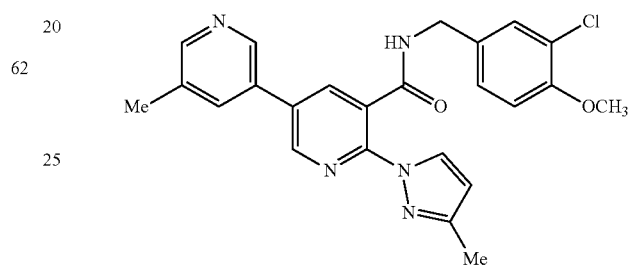
66
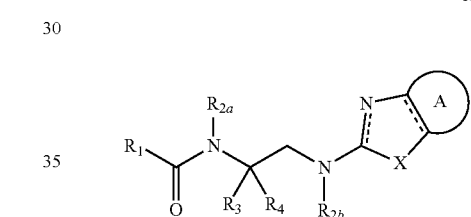
67
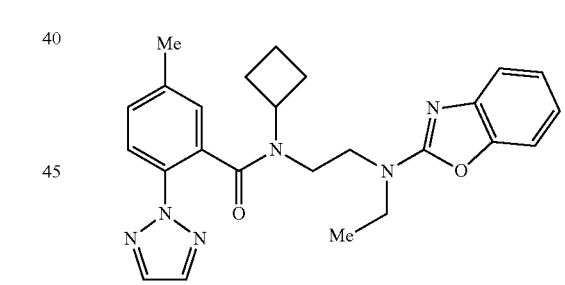
68
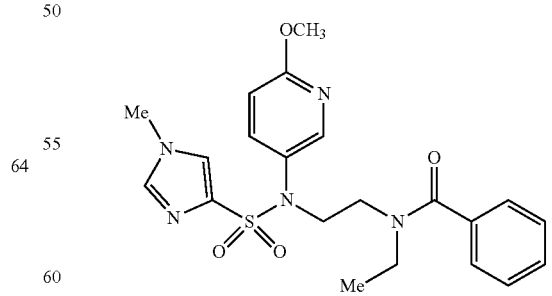
69
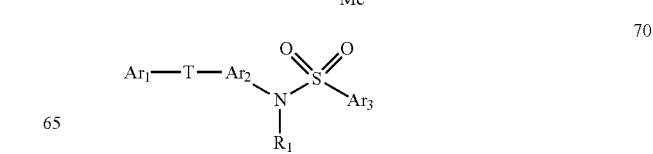
70

-continued

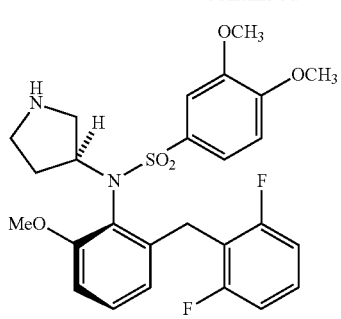
71

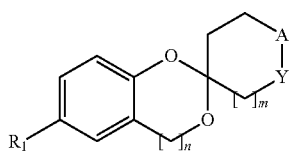
72

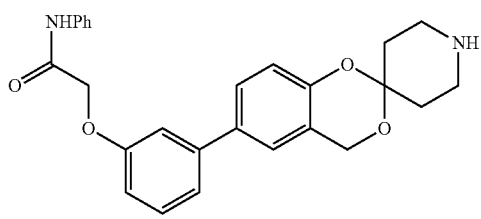
73

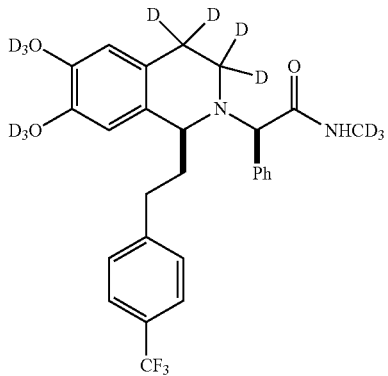
74

In some embodiments, the OX1R antagonist of the present invention is selected from 2-pyridyloxy-3-substituted-4-nitrile orexin receptor antagonists that are disclosed in WO 2014066196. In some embodiments, the OX1R antagonist of the present invention is selected from the group consisting of:

3-methyl-2-{[(3R,6R)-6-methyl-1-{[2-(2H-1,2,3-triazol-2-1)phenyl]carbonyl}piperidin-3-yl]oxy}pyridine-4-carbonitrile;

2-{[(3R,6R)-1-{[6-methoxy-2-(2H-1,2,3-triazol-2-yl)pyridin-3-yl]carbonyl}-6-methylpiperidin-3-yl]oxy}-3-methylpyridine-4-carbonitrile;

2-{[(3R,6R)-1-{[5-chloro-2-(2H-1,2,3-triazol-2-yl)phenyl]carbonyl}-6-ethylpiperidin-3-yl]oxy}-3-methylpyridine-4-carbonitrile;

2-{[(3R,6R)-1-{[4-chloro-2-(2H-1,2,3-triazol-2-yl)phenyl]carbonyl}-6-ethylpiperidin-3-yl]oxy}-3-methylpyridine-4-carbonitrile;

2-({(3R,6R)-1-[(2-cyclopropyl-6-methoxypyridin-3-yl)carbonyl]-6-methylpiperidin-3-yl}oxy)-3-methylpyridine-4-carbonitrile;

3-methyl-2-{[(3R,6R)-6-methyl-1-{[5-methyl-2-(2H-1,2,3-triazol-2-yl)phenyl]carbonyl}piperidin-3-yl]oxy}pyridine-4-carbonitrile;

2-{[(3R,6R)-1-{[4-methoxy-2-(2H-1,2,3-triazol-2-yl)phenyl]carbonyl}-6-methylpiperidin-3-yl]oxy}-3-methylpyridine-4-carbonitrile;

3-methyl-2-{[(3R,6R)-6-methyl-1-{[4-methyl-2-(2H-1,2,3-triazol-2-yl)phenyl]carbonyl}piperidin-3-yl]oxy}pyridine-4-carbonitrile;

2-{[(3R,6R)-1-{[4-fluoro-2-(2H-1,2,3-triazol-2-yl)phenyl]carbonyl}-6-methylpiperidin-3-yl]oxy}-3-methylpyridine-4-carbonitrile;

3-methyl-2-{[(3R,6R)-6-methyl-1-{[4-(2H-1,2,3-triazol-2-yl)pyridin-3-yl]carbonyl}piperidin-3-yl]oxy}pyridine-4-carbonitrile;

2-{[(3R,6R)-1-{[2-fluoro-6-(2H-1,2,3-triazol-2-yl)phenyl]carbonyl}-6-methylpiperidin-3-yl]oxy}-3-methylpyridine-4-carbonitrile;

2-{[(3R,6R)-1-{[3-fluoro-2-(2H-1,2,3-triazol-2-yl)phenyl]carbonyl}-6-methylpiperidin-3-yl]oxy}-3-methylpyridine-4-carbonitrile;

3-methyl-2-{[(3R,6R)-6-methyl-1-{[3-methyl-2-(2H-1,2,3-triazol-2-yl)phenyl]carbonyl}piperidin-3-yl]oxy}pyridine-4-carbonitrile;

2-{[(3R,6R)-1-{[2-methoxy-6-(2H-1,2,3-triazol-2-yl)phenyl]carbonyl}-6-methylpiperidin-3-yl]oxy}-3-methylpyridine-4-carbonitrile;

3-methyl-2-{[(3R,6R)-6-methyl-1-{[2-methyl-6-(2H-1,2,3-triazol-2-yl)phenyl]carbonyl}piperidin-3-yl]oxy}pyridine-4-carbonitrile;

2-({(3R,6R)-1-[(2-cyclopropylphenyl)carbonyl]-6-methylpiperidin-3-yl}oxy)-3-methylpyridine-4-carbonitrile;

3-methyl-2-{[(3R,6R)-6-methyl-1-{[2-(trifluoromethyl)phenyl]carbonyl}piperidin-3-yl]oxy}pyridine-4-carbonitrile;

2-{[(3R,6R)-1-{[2-fluoro-6-(1,3-thiazol-2-yl)phenyl]carbonyl}-6-methylpiperidin-3-yl]oxy}-3-methylpyridine-4-carbonitrile;

2-({(3R,6R)-1-[(2-ethoxyphenyl)carbonyl]-6-methylpiperidin-3-yl}oxy)-3-methylpyridine-4-carbonitrile;

3-methyl-2-({(3R,6R)-6-methyl-1-[(4-phenylisothiazol-5-yl)carbonyl]piperidin-3-yl}oxy)pyridine-4-carbonitrile;

3-methyl-2-{[(3R,6R)-6-methyl-1-{[2-(1-methylethoxy)phenyl]carbonyl}piperidin-3-yl]oxy}pyridine-4-carbonitrile;

2-{[(3R,6R)-1-{[2-fluoro-6-(1,3-thiazol-4-yl)phenyl]carbonyl}-6-methylpiperidin-3-yl]oxy}-3-methylpyridine-4-carbonitrile;

3-methyl-2-({(3R,6R)-6-methyl-1-[(3-phenylpyridin-4-yl)carbonyl]piperidin-3-yl}oxy)pyridine-4-carbonitrile;

3-methyl-2-{[(3R,6R)-6-methyl-1-{[3-(1,3-thiazol-4-yl)pyridin-2-yl]carbonyl}piperidin-3-yl]oxy}pyridine-4-carbonitrile;

2-{[(3R,6R)-1-{[2-fluoro-5-(1,3-thiazol-5-yl)pyridin-4-yl]carbonyl}-6-methylpiperidin-3-yl]oxy}-3-methylpyridine-4-carbonitrile;

2-{[(3R,6R)-1-{[5-fluoro-2-(1,3-thiazol-4-yl)phenyl]carbonyl}-6-methylpiperidin-3-yl]oxy}-3 methylpyridine-4-carbonitrile;

3-methyl-2-{[(3R,6R)-6-methyl-1-{[2-(1,3-oxazol-2-yl)phenyl]carbonyl}piperidin-3-yl]oxy}pyridine-4-carbonitrile;

2-{[(3R,6R)-1-{[5-fluoro-2-(1,3-thiazol-2-yl)phenyl]carbonyl}-6-methylpiperidin-3-yl]oxy}-3 methylpyridine-4-carbonitrile;

3-methyl-2-({(3R,6R)-6-methyl-1-[(2-pyrrolidin-1-ylphenyl)carbonyl]piperidin-3-yl}oxy)pyridine-4-carbonitrile;

3-methyl-2-({(3R,6R)-6-methyl-1-[(2-phenoxyphenyl)carbonyl]piperidin-3-yl}oxy)pyridine-4-carbonitrile;
3-methyl-2-{[(3R,6R)-6-methyl-1-{[2-(1,3-thiazol-4-yl)thiophen-3-yl]carbonyl}piperidin-3-yl]oxy}pyridine-4-carbonitrile;
3-methyl-2-{[(3R,6R)-6-methyl-1-{[2-(1,3-thiazol-2-yl)thiophen-3-yl]carbonyl}piperidin-3-yl]oxy}pyridine-4-carbonitrile;
3-methyl-2-{[(3R,6R)-6-methyl-1-{[2-(1,3-thiazol-4-yl)phenyl]carbonyl}piperidin-3-yl]oxy}pyridine-4-carbonitrile;
2-{[(3R,6R)-1-{[4-fluoro-2-(1,3-thiazol-2-yl)phenyl]carbonyl}-6-methylpiperidin-3-yl]oxy}-3 methylpyridine-4-carbonitrile;
2-{[(3R,6R)-1-{[5-fluoro-2-(1,3-thiazol-2-yl)pyridin-3-yl]carbonyl}-6-methylpiperidin-3-yl]oxy}-3-methylpyridine-4-carbonitrile;
3-methyl-2-{[(3R,6R)-6-methyl-1-{[2-(1-methyl-1H-pyrazol-4-yl)phenyl]carbonyl}piperidin-3 yl]oxy}pyridine-4-carbonitrile;
3-methyl-2-{[(3R,6R)-6-methyl-1-{[3-(1,3-thiazol-2-yl)thiophen-2-yl]carbonyl}piperidin-3-yl]oxy}pyridine-4-carbonitrile;
3-methyl-2-{[(3R,6R)-6-methyl-1-{[3-(1,3-thiazol-4-yl)thiophen-2-yl]carbonyl}piperidin-3-yl]oxy}pyridine-4-carbonitrile;
3-methyl-2-{[(3R,6R)-6-methyl-1-{[242H-1,2,3-triazol-2-yl)thiophen-3-yl]carbonyl}piperidin 3-yl]oxy}pyridine-4-carbonitrile;
3-methyl-2-{[(3R,6R)-6-methyl-1-{[2-(5-methyl-2H-tetrazol-2-yl)phenyl]carbonyl}piperidin-3 yl]oxy}pyridine-4-carbonitrile;
2-{[(3R,6R)-1-{[5-(4-fluorophenyl)-2-methyl-1,3-thiazol-4-yl]carbonyl}-6-methylpiperidin-3-yl]oxy}-3-methylpyridine-4-carbonitrile;
3-methyl-2-{[(3R,6R)-6-methyl-1-{[2-(5-methyl-1,2,4-oxadiazol-3-yl)phenyl]carbonyl}piperidin-3-yl]oxy}pyridine-4-carbonitrile;
3-methyl-2-{[(3R,6R)-6-methyl-1-{[2-(4-methyl-1H-pyrazol-1-yl)phenyl]carbonyl}piperidin-3-yl]oxy}pyridine-4-carbonitrile;
3-methyl-2-{[(3R,6R)-6-methyl-1-{[2-(1,3-thiazol-2-yl)phenyl]carbonyl}piperidin-3-yl]oxy}pyridine-4-carbonitrile;
3-methyl-24{(3R,6R)-6-methyl-1-[(1-methyl-3-phenyl-1H-pyrazol-4-yl)carbonyl]piperidin-3-yl}oxy)pyridine-4-carbonitrile;
3-methyl-2-{[(3R,6R)-6-methyl-1-{[1-methyl-3-(1,3-thiazol-2-yl)-1H-pyrazol-4-yl]carbonyl}piperidin-3-yl]oxy}pyridine-4-carbonitrile;
3-methyl-24{(3R,6R)-6-methyl-1-[(3-methyl-5-phenylisothiazol-4-yl)carbonyl]piperidin-3-yl}oxy)pyridine-4-carbonitrile;
2-({(3R,6R)-1-[(6-methoxy-2,4'-bipyridin-3-yl)carbonyl]-6-methylpiperidin-3-yl}oxy)-3-methylpyridine-4-carbonitrile;
2-{[(3R,6R)-1-{[2-(6-methoxypyridin-3-yl)phenyl]carbonyl}-6-methylpiperidin-3-yl]oxy}-3-methylpyridine-4-carbonitrile;
3-methyl-24{(3R,6R)-6-methyl-1-[(4-phenylisothiazol-3-yl)carbonyl]piperidin-3-yl}oxy)pyridine-4-carbonitrile;
2-({(3R,6R)-1-[(2-cyclopropyl-4-methylphenyl)carbonyl]-6-methylpiperidin-3-yl}oxy)-3-methylpyridine-4-carbonitrile;
2-({(3R,6R)-1-[(2-cyclopropyl-4-methoxyphenyl)carbonyl]-6-methylpiperidin-3-yl}oxy)-3-methylpyridine-4-carbonitrile;
2-({(3R,6R)-1-[(2-cyclopropyl-4-fluorophenyl)carbonyl]-6-methylpiperidin-3-yl}oxy)-3-methylpyridine-4-carbonitrile;
2-{[(3R,6R)-1-{[5-(hydroxymethyl)biphenyl-2-yl]carbonyl}-6-methylpiperidin-3-yl]oxy}-3-methylpyridine-4-carbonitrile;
3-methyl-2-{[(3R,6R)-6-methyl-1-{[4-(2H-1,2,3-triazol-2-yl)isothiazol-3-yl]carbonyl}piperidin-3-yl]oxy}pyridine-4-carbonitrile;
2-({(3R,6R)-1-[(5-fluoro-2-pyridin-2-ylphenyl)carbonyl]-6-methylpiperidin-3-yl}oxy)-3-methylpyridine-4-carbonitrile;
3-methyl-2-({(3R,6R)-6-methyl-1-[(2-methyl-5-phenyl-1,3-thiazol-4-yl)carbonyl]piperidin-3-yl}oxy)pyridine-4-carbonitrile;
3-methyl-2-{[(3R,6R)-6-methyl-1-{[2-(3-methyl-1,2,4-oxadiazol-5-yl)phenyl]carbonyl}piperidin-3-yl]oxy}pyridine-4-carbonitrile;
2-({(3R,6R)-1-[(2-ethylphenyl)carbonyl]-6-methylpiperidin-3-yl}oxy)-3-methylpyridine-4-carbonitrile;
3-methyl-2-({(3R,6R)-6-methyl-1-[(2-phenylpyridin-3-yl)carbonyl]piperidin-3-yl}oxy)pyridine-4-carbonitrile;
3-methyl-2-{[(3R,6R)-6-methyl-1-{[2-(methylsulfanyl)phenyl]carbonyl}piperidin-3-yl]oxy}pyridine-4-carbonitrile;
3-methyl-2-{[(3R,6R)-6-methyl-1-{[2-(trifluoromethoxy)phenyl]carbonyl}piperidin-3-yl]oxy}pyridine-4-carbonitrile;
3-methyl-2-({(3R,6R)-6-methyl-1-[(2-pyridin-2-ylcyclopent-1-en-1-yl)carbonyl]piperidin-3-yl}oxy)pyridine-4-carbonitrile;
2-{[(3R,6R)-1-{[4-(fluoromethoxy)-2-(2H-1,2,3-triazol-2-yl)phenyl]carbonyl}-6-methylpiperidin-3-yl]oxy}-3-methylpyridine-4-carbonitrile;
2-{[(3R,6R)-1-{[4-(difluoromethoxy)-2-(2H-1,2,3-triazol-2-yl)phenyl]carbonyl}-6-methylpiperidin-3-yl]oxy}-3-methylpyridine-4-carbonitrile;
2-({(3R,6R)-1-[(2-cyclobutyl-6-methoxypyridin-3-yl)carbonyl]-6-methylpiperidin-3-yl}oxy)-3-methylpyridine-4-carbonitrile;
2-{[(3R,6R)-1-{[6-chloro-4-(2H-1,2,3-triazol-2-yl)pyridin-3-yl]carbonyl}-6-methylpiperidin-3-yl]oxy}-3-methylpyridine-4-carbonitrile;
2-({(3R,6R)-1-[(2-ethoxypyridin-3-yl)carbonyl]-6-methylpiperidin-3-yl}oxy)-3-methylpyridine-4-carbonitrile;
2-{[(3R,6R)-1-{[5-fluoro-2-(2H-1,2,3-triazol-2-yl)phenyl]carbonyl}-6-methylpiperidin-3-yl]oxy}-3-methylpyridine-4-carbonitrile;
3-methyl-2-{[(3R,6R)-6-methyl-1-{[2-(2H-tetrazol-2-yl)phenyl]carbonyl}piperidin-3-yl]oxy}pyridine-4-carbonitrile;
2-{[(3R,6R)-1-{[5-cyano-2-(2H-1,2,3-triazol-2-yl)phenyl]carbonyl}-6-methylpiperidin-3-yl]oxy}-3-methylpyridine-4-carbonitrile;
2-{[(3R,6R)-1-{[6-chloro-2-(2H-1,2,3-triazol-2-yl)pyridin-3-yl]carbonyl}-6-methylpiperidin-3-yl]oxy}-3-methylpyridine-4-carbonitrile;
2-({(3R,6R)-1-[(2,6-dimethoxypyridin-3-yl)carbonyl]-6-methylpiperidin-3-yl}oxy)-3-methylpyridine-4-carbonitrile;
3-methyl-2-{[(3R,6R)-6-methyl-1-{[2-(pyrimidin-2-yl)phenyl]carbonyl}piperidin-3-yl]oxy}pyridine-4-carbonitrile;
3-methyl-2-({(3R,6R)-6-methyl-1-[(3-pyrimidin-2-ylthiophen-2-yl)carbonyl]piperidin-3-yl}oxy)pyridine-4-carbonitrile;

3-methyl-2-({(3R,6R)-6-methyl-1-[(4-methyl-2-yrimidin-2-ylphenyl)carbonyl]piperidin-3-yl}oxy)pyridine-4-carbonitrile;

3-methyl-2-({(3R,6R)-6-methyl-1-[(2-yrimidin-2-ylthiophen-3-yl)carbonyl]piperidin-3-yl}oxy)pyridine-4-carbonitrile;

2-({(3R,6R)-1-[(6-methoxy-2-phenylpyridin-3-yl)carbonyl]-6-methylpiperidin-3-yl}oxy)-3-methylpyridine-4-carbonitrile;

2-{[(3R,6R)-1-{[6-methoxy-2-(1-methyl-1H-pyrazol-5-yl)pyridin-3-yl]carbonyl}-6-methylpiperidin-3-yl]oxy}-3-methylpyridine-4-carbonitrile;

2-{[(3R,6R)-1-{[6-methoxy-2-(1-methyl-1H-pyrazol-4-yl)pyridin-3-yl]carbonyl}-6-methylpiperidin-3-yl]oxy}-3-methylpyridine-4-carbonitrile;

2-{[(3R,6R)-1-{[6-methoxy-2-(1-methyl-1H-pyrazol-3-yl)pyridin-3-yl]carbonyl}-6-methylpiperidin-3-yl]oxy}-3-methylpyridine-4-carbonitrile;

2-({(3R,6R)-1-[(6-methoxy-2,3'-bipyridin-3-yl)carbonyl]-6-methylpiperidin-3-yl}oxy)-3-methylpyridine-4-carbonitrile;

2-({(3R,6R)-1-[(6-methoxy-2,2'-bipyridin-3-yl)carbonyl]-6-methylpiperidin-3-yl}oxy)-3-methylpyridine-4-carbonitrile;

2-{[(3R,6R)-1-{[6-Methoxy-2-(methylsulfanyl)pyridin-3-yl]carbonyl}-6-methylpiperidin-3-yl]oxy}-3-methylpyridine-4-carbonitrile;

2-{[(3R,6R)-1-{[6-methoxy-4-(2H-1,2,3riazol-2-yl)pyridin-3-yl]carbonyl}-6-methylpiperidin 3-yl]oxy}-3-methylpyridine-4-carbonitrile;

3-methyl-2-{[(3R,6R)-6-methyl-{[6-(methylsulfanyl)-2-(2H-1,2,3-triazol-2-yl)pyridin-3-yl]carbonyl}piperidin-3-yl]oxy}pyridine-4-carbonitrile;

2-{[(3R,6R)-1-{[2-(dimethylamino)-6-methoxypyridin-3-yl]carbonyl}-6-methylpiperidin-3-yl]oxy}-3-methylpyridine-4-carbonitrile;

2-{[(3R,6R)-1-{[6-(fluoromethoxy)-2-(2H-1,2,3-triazol-2-yl)pyridin-3-yl]carbonyl}-6-methylpiperidin-3-yl]oxy}-3-methylpyridine-4-carbonitrile;

2-{[(3R,6R)-1-{[6-bromo-2-(2H-1,2,3-triazol-2-yl)pyridin-3-yl]carbonyl}-6-methylpiperidin-3 yl]oxy}-3-methylpyridine-4-carbonitrile;

2-{[(3R,6R)-1-{[6-ethenyl-2-(2H-1,2,3 riazol-2-yl)pyridin-3-yl]carbonyl}-6-methylpiperidin-yl]oxy}-3-methylpyridine-4-carbonitrile;

3-chloro-2-{[(3R,6R)-6-methyl-1-{[2-(2H-1,2,3-triazol-2-yl)phenyl]carbonyl}piperidin-3-yl]oxy}pyridine-4-carbonitrile;

3-cyclopropyl-2-{[(3R,6R)-6-methyl-1-{[2-(2H-1,2,3-triazol-2-yl)phenyl]carbonyl}piperidin-3 yl]oxy}pyridine-4-carbonitrile;

3-ethyl-2-{[(3R,6R)-6-methyl-1-{[2-(2H-1,2,3-triazol-2-yl)phenyl]carbonyl}piperidin-3-yl]oxy}pyridine-4-carbonitrile;

2-{[(3R,6R)-6-methyl-1-{[2-(2H-1,2,3-triazol-2-yl)phenyl]carbonyl}piperidin-3-yl]oxy}pyridine-3,4-dicarbonitrile;

3-(methylsulfanyl)-2-{[(3R,6R)-6-methyl-1-{[2-(2H-1,2,3-triazol-2-yl)phenyl]carbonyl}piperidin-3-yl]oxy}pyridine-4-carbonitrile;

3-methoxy-2-{[(3R,6R)-6-methyl-1-{[2-(2H-1,2,3-triazol-2-yl)phenyl]carbonyl}piperidin-3-yl]oxy}pyridine-4-carbonitrile;

2-{[(3R,6R)-1-{[3-fluoro-2-(2H-1,2,3-triazol-2-yl)phenyl]carbonyl}-6-methylpiperidin-3-yl]oxy}-3-methoxypyridine-4-carbonitrile;

2-{[(3R,6R)-1-{[4-fluoro-2-(2H-1,2,3-triazol-2-yl)phenyl]carbonyl}-6-methylpiperidin-3-yl]oxy}-3-methoxypyridine-4-carbonitrile;

2-{[(3R,6R)-1-{[5-fluoro-2-(2H-1,2,3-triazol-2-yl)phenyl]carbonyl}-6-methylpiperidin-3-yl]oxy}-3-methoxypyridine-4-carbonitrile;

2-{[(3R,6R)-1-{[2-fluoro-6-(2H-1,2,3-triazol-2-yl)phenyl]carbonyl}-6-methylpiperidin-3-yl]oxy}-3-methoxypyridine-4-carbonitrile;

3-methoxy-2-{[(3R,6R)-6-methyl-1-{[3-methyl-2-(2H-1,2,3-triazol-2-yl)phenyl]carbonyl}piperidin-3-yl]oxy}pyridine-4-carbonitrile;

3-methoxy-2-{[(3R,6R)-6-methyl-1-{[4-methyl-2-(2H-1,2,3-triazol-2-yl)phenyl]carbonyl}piperidin-3-yl]oxy}pyridine-4-carbonitrile;

3-methoxy-2-{[(3R,6R)-6-methyl-1-{[5-methyl-2-(2H-1,2,3-triazol-2-yl)phenyl]carbonyl}piperidin-3-yl]oxy}pyridine-4-carbonitrile;

3-methoxy-2-{[(3R,6R)-1-{[6-methoxy-2-(2H-1,2,3-triazol-2-yl)pyridin-3-yl]carbonyl}-6-methylpiperidin-3-yl]oxy}pyridine-4-carbonitrile;

2-({(3R,6R)-1-[(2-cyclobutylphenyl)carbonyl]-6-methylpiperidin-3-yl}oxy)-3-methoxypyridine-4-carbonitrile;

3-methoxy-2-{[(3R,6R)-6-methyl-1-{[2-(2H-1,2,3-triazol-2-yl)thiophen-3-yl]carbonyl}piperidin-3-yl]oxy}pyridine-4-carbonitrile;

3-methoxy-24 {(3R,6R)-6-methyl-1-[(2-pyrimidin-2-ylphenyl)carbonyl]piperidin-3-yl}oxy)pyridine-4-carbonitrile;

3-methoxy-24 {(3R,6R)-6-methyl-1-[(2-pyrimidin-2-ylthiophen-3-yl)carbonyl]piperidin-3-yl}oxy)pyridine-4-carbonitrile;

methyl 4-cyano-2-{[(3R,6R)-1-{[3-fluoro-2-(pyrimidin-2-yl)phenyl]carbonyl}-6-methylpiperidin-3-yl]oxy}pyridine-3-carboxylate-2-({(3R,6R)-1-[(4-fluoro-2ˆyrimidin-2-ylphenyl)carbonyl]-6-methylpiperidin-3-yl}oxy)-3-methoxypyridine-4-carbonitrile;

2-({(3R,6R)-1-[(5-fluoro-2ˆyrimidin-2-ylphenyl)carbonyl]-6-methylpiperidin-3-yl}oxy)-3-methoxypyridine-4-carbonitrile;

2-({(3R,6R)-1-[(2-fluoro-6ˆyrimidin-2-ylphenyl)carbonyl]-6-methylpiperidin-3-yl}oxy)-3-methoxypyridine-4-carbonitrile;

3-methoxy-2-({(3R,6R)-1-[(6-methoxy-2-pyrimidin-2-ylpyridin-3-yl)carbonyl]-6-methylpiperidin-3-yl}oxy)pyridine-4-carbonitrile;

3-methyl-2-{[(3R,6R)-6-methyl-1-{[2-(1-methylethoxy)pyridin-3-yl]carbonyl}piperidin-3-yl]oxy}pyridine-4-carbonitrile; and 3-methoxy-2-{[(3R,6R)-6-methyl-1-{[2-(2H-tetrazol-2-yl)phenyl]carbonyl}piperidin-3-yl]oxy}pyridine-4-carbonitrile;

and pharmaceutically acceptable salts thereof.

In some embodiments, the OX1R antagonist of the present invention is selected from 2-pyridylamino-4-nitrile-piperidinyl orexin receptor antagonists that are disclosed in WO 2014085208 A1. In some embodiments, the OX1R antagonist of the present invention is selected from the group consisting of:

2-(((3R,6R)-1-(2-(2H-1,2,3-triazol-2-yl)benzoyl)-6-methylpiperidin-3-yl)amino)isonicotinonitrile;

3-methoxy-2-{[(3R,6R)-6-methyl-1-{[2-(2H-1,2,3-triazol-2-yl)phenyl]carbonyl}piperidin-3-yl]amino}pyridine-4-carbonitrile;

2-(((3R,6R)-1-(2-(2H etrazol-2-yl)benzoyl)-6-methylpiperidin-3-yl)amino)isonicotinonitrile;

2-(((3R,6R)-1-(2-(2H-1,2,3-triazol-2-yl)benzoyl)-6-methylpiperidin-3-yl)amino)-3-methylisonicotinonitrile;

3-methyl-2-{[(3R,6R)-6-methyl-1-{[2-(2H-tetrazol-2-yl)phenyl]carbonyl}piperidin-3-yl]amino}pyridine-4-carbonitrile;

2-((3R,6R)-1-(2-(2H-1,2,3-triazol-2-yl)thiophene-3-carbonyl)-6-methylpiperidin-3-ylamino)-3 methoxyisonicotinonitrile;

3-methoxy-2-((3R,6R)-6-methyl-1-(2-(yrimidin-2-yl)thiophene-3-carbonyl)piperidin-3-ylamino)isonicotinonitrile;

2-(((3R,6R)-1-(2-(2H-1,2,3-triazol-2-yl)benzoyl)-6-methylpiperidin-3-yl)(methyl)amino)isonicotinonitrile;

2-{methyl[(3R,6R)-6-methyl-1-{[2-(2H-tetrazol-2-yl)phenyl]carbonyl}piperidin-3-yl]amino}pyridine-4-carbonitrile;

3-methoxy-2-{methyl[(3R,6R)-6-methyl-1-{[2-(2H-1,2,3-triazol-2-yl)thiophen-3-yl]carbonyl}piperidin-3-yl]amino}pyridine-4-carbonitrile;

3-methoxy-2-(methyl {(3R,6R)-6-methyl-1-[(2-pyrimidin-2-ylthiophen-3-yl)carbonyl]piperidin 3-yl}amino)pyridine-4-carbonitrile;

2-{ethyl[(3R,6R)-6-methyl-1-{[2-(2H-1,2,3-triazol-2-yl)phenyl]carbonyl}piperidin-3-yl]amino}pyridine-4-carbonitrile;

2-{[(3R,6R)-6-methyl-1-{[2-(2H-1,2,3-triazol-2-yl)phenyl]carbonyl}piperidin-3-yl](prop-2-en-1-yl)amino}pyridine-4-carbonitrile;

2-{[(3R,6R)-6-methyl-1-{[2-(2H-1,2,3-triazol-2-yl)phenyl]carbonyl}piperidin-3-yl](propyl)amino}pyridine-4-carbonitrile;

N-((3R,6R)-1-(2-(2H-1,2,3-triazol-2-yl)benzoyl)-6-methylpiperidin-3-yl)-N-(4-cyanopyridin-2 yl)acetamide;

methyl 4-cyano-2-{[(3R,6R)-6-methyl-1-{[2-(2H-1,2,3-triazol-2-yl)phenyl]carbonyl}piperidine-3-yl]amino}pyridine-3-carboxylate;

methyl 4-cyano-2-({(3R,6R)-6-methyl-1-[(2-pyrimidin-2-ylphenyl)carbonyl]piperidin-3-yl}amino)pyridine-3-carboxylate;

and pharmaceutically acceptable salts thereof.

In some embodiments, the OX1R antagonist of the present invention is selected from 2-pyridyloxy-4-nitrile orexin receptor antagonists that are disclosed in WO 2013059222 A1.

In some embodiments, the OX1R antagonist of the present invention is selected from the group consisting of 2-{[(3R,6R)-6-methyl-1-{[2-(2H-1,2,3-triazol-2-yl)phenyl]carbonyl}piperidin-3-yl]oxy}pyridine-4-carbonitrile;

2-({(3R,6R)-6-methyl-1-[(2-pyrimidin-2-ylphenyl)carbonyl]piperidin-3-yl}oxy)pyridine-4-carbonitrile;

2-{[(3R,6R)-6-methyl-1-{[2-(5-methyl-1,2,4-oxadiazol-3-yl)phenyl]carbonyl}piperidin-3-yl]oxy}pyridine-4-carbonitrile;

2-{[(3R,6R)-6-methyl-1-{[2-methyl-6-(2H-1,2,3-triazol-2-yl)phenyl]carbonyl}piperidin-3-yl]oxy}pyridine-4-carbonitrile;

2-{[(3R,6R)-6-methyl-1-{[3-methyl-2-(2H-1,2,3-triazol-2-yl)phenyl]carbonyl}piperidin-3-yl]oxy}pyridine-4-carbonitrile;

2-{[(3R,6R)-1-{[3-fluoro-2-(2H-1,2,3-triazol-2-yl)phenyl]carbonyl}-6-methylpiperidin-3-yl]oxy}pyridine-4-carbonitrile;

2-{[(3R,6R)-1-{[4-chloro-2-(2H-1,2,3-triazol-2-yl)phenyl]carbonyl}-6-methylpiperidin-3-yl]oxy}pyridine-4-carbonitrile;

2-{[(3R,6R)-1-{[4-fluoro-2-(2H-1,2,3-triazol-2-yl)phenyl]carbonyl}-6-methylpiperidin-3-yl]oxy}pyridine-4-carbonitrile;

2-{[(3R,6R)-6-methyl-1-{[4-methyl-2-(2H-1,2,3-triazol-2-yl)phenyl]carbonyl}piperidin-3-yl]oxy}pyridine-4-carbonitrile;

2-{[(3R,6R)-6-methyl-1-{[2-(2H-1,2,3-triazol-2-yl)thiophen-3-yl]carbonyl}piperidin-3-yl]oxy}pyridine-4-carbonitrile;

2-{[(3R,6R)-6-methyl-1-{[4-(2H-1,2,3-triazol-2-yl)isothiazol-3-yl]carbonyl}piperidin-3-yl]oxy}pyridine-4-carbonitrile;

2-{[(3R,6R)-6-methyl-1-{[1-methyl-3-(2H-1,2,3-triazol-2-yl)-1H-pyrazol-4-yl]carbonyl}piperidin-3-yl]oxy}pyridine-4-carbonitrile;

2-{[(3R,6R)-6-methyl-1-{[3-methyl-5-(2H-1,2,3-triazol-2-yl)isothiazol-4-yl]carbonyl}piperidin-3-yl]oxy}pyridine-4-carbonitrile;

2-{[(3R,6R)-6-methyl-1-{[3-(2H-1,2,3-triazol-2-yl)thiophen-2-yl]carbonyl}piperidin-3-yl]oxy}pyridine-4-carbonitrile;

2-{[(3R,6R)-1-{[5-bromo-2-(2H-1,2,3-triazol-2-yl)phenyl]carbonyl}-6-methylpiperidin-3-yl]oxy}pyridine-4-carbonitrile;

2-{[(3R,6R)-1-{[5-chloro-2-(2H-1,2,3-triazol-2-yl)phenyl]carbonyl}-6-methylpiperidin-3-yl]oxy}pyridine-4-carbonitrile;

2-{[(3R,6R)-1-{[6-methoxy-2-(2H-1,2,3-triazol-2-yl)pyridin-3-yl]carbonyl}-6-methylpiperidin-3-yl]oxy}pyridine-4-carbonitrile;

3-({(2R,5R)-5-[(4-cyanopyridin-2-yl)oxy]-2-methylpiperidin-1-yl}carbonyl)-4-(2H-1,2,3-triazol-2-yl)benzamide;

2-{[(3R,6R)-1-{[4-cyano-2-(2H-1,2,3-triazol-2-yl)phenyl]carbonyl}-6-methylpiperidin-3-yl]oxy}pyridine-4-carbonitrile;

2-({(3R,6R)-1-[(2-cyclopropyl-6-methoxypyridin-3-yl)carbonyl]-6-methylpiperidin-3-yl}oxy)pyridine-4-carbonitrile;

2-{[(3R,6R)-1-{[4-ethoxy-2-(2H-1,2,3-triazol-2-yl)phenyl]carbonyl}-6-methylpiperidin-3-yl]oxy}pyridine-4-carbonitrile;

2-{[(3R,6R)-1-{[2-fluoro-6-(2H-1,2,3-triazol-2-yl)phenyl]carbonyl}-6-methylpiperidin-3-yl]oxy}pyridine-4-carbonitrile;

2-{[(3R,6R)-1-{[4-(fluoromethoxy)-2-(2H-1,2,3-triazol-2-yl)phenyl]carbonyl}-6-methylpiperidin-3-yl]oxy}pyridine-4-carbonitrile;

2-{[(3R,6R)-1-{[4-(difluoromethoxy)-2-(2H-1,2,3-triazol-2-yl)phenyl]carbonyl}-6-methylpiperidin-3-yl]oxy}pyridine-4-carbonitrile;

2-{[(3R,6R)-1-{[4-(2-hydroxyethoxy)-2-(2H-1,2,3-triazol-2-yl)phenyl]carbonyl}-6-methylpiperidin-3-yl]oxy}pyridine-4-carbonitrile;

2-{[(3R,6R)-6-methyl-1-{[6-methyl-2-(2H-1,2,3-triazol-2-yl)pyridin-3-yl]carbonyl}piperidin-3 yl]oxy}pyridine-4-carbonitrile;

2-{[(3R,6R)-6-methyl-1-{[2-(2H-1,2,3-triazol-2-yl)-6-(trifluoromethyl)pyridin-3-yl]carbonyl}piperidin-3-yl]oxy}pyridine-4-carbonitrile;

2-({(3R,6R)-1-[(2-chloro-6-methoxypyridin-3-yl)carbonyl]-6-methylpiperidin-3-yl}oxy)pyridine-4-carbonitrile;

2-{[(3R,6R)-1-{[4-chloro-2-(2H-1,2,3-triazol-2-yl)phenyl]carbonyl}-6-methylpiperidin-3-yl]oxy}pyridine-4-carbonitrile;

2-{[(3R,6R)-6-methyl-1-{[2-(2H-tetrazol-2-yl)phenyl]carbonyl}piperidin-3-yl]oxy}pyridine-4-carbonitrile;

2-({(3R,6R)-6-methyl-1-[(3-pyrimidin-2-ylthiophen-2-yl)carbonyl]piperidin-3-yl}oxy)pyridine-4-carbonitrile;

2-({(3R,6R)-6-methyl-1-[(2-pyrimidin-2-ylthiophen-3-yl)carbonyl]piperidin-3-yl}oxy)pyridine-4-carbonitrile;

2-({(3R,6R)-1-[(3-fluoro-2-pyrimidin-2-ylphenyl)carbonyl]-6-methylpiperidin-3-yl}oxy)pyridine-4-carbonitrile;
2-({(3R,6R)-1-[(4-fluoro-2-pyrimidin-2-ylphenyl)carbonyl]-6-methylpiperidin-3-yl}oxy)pyridine-4-carbonitrile;
2-({(3R,6R)-1-[(5-fluoro-2-pyrimidin-2-ylphenyl)carbonyl]-6-methylpiperidin-3-yl}oxy)pyridine-4-carbonitrile; and
2-({(3R,6R)-1-[(2-fluoro-6-pyrimidin-2-ylphenyl)carbonyl]-6-methylpiperidin-3-yl}oxy)pyridine-4-carbonitrile;
and pharmaceutically acceptable salts thereof.

In some embodiments, the OX1R antagonist of the present invention is selected from 2-pyridyloxy-4-ester orexin receptor antagonists that are disclosed in WO 2014099696 A1. In some embodiments, the OX1R antagonist of the present invention is selected from the group consisting of:
methyl 2-{[(3R,6R)-6-methyl-1-{[2-(2H-1,2,3-triazol-2-yl)phenyl]carbonyl}piperidin-3-yl]oxy}pyridine-4-carboxylate;
2-{[(3R,6R)-6-methyl-1-{[2-(2H-1,2,3-triazol-2-yl)phenyl]carbonyl}piperidin-3-yl]oxy}pyridine-4-carboxylic acid;
methyl 2-{[(3R,6R)-6-methyl-1-{[2-(2H-1,2,3-triazol-2-yl)phenyl]carbonyl}piperidin-3-yl]oxy}-5-(trifluoromethyl)pyridine-4-carboxylate;
methyl 5-bromo-2-{[(3R,6R)-6-methyl-1-{[2-(2H-1,2,3-triazol-2-yl)phenyl]carbonyl}piperidin-3-yl]oxy}pyridine-4-carboxylate;
methyl 3-chloro-2-{[(3R,6R)-6-methyl-1-{[2-(2H-1,2,3-triazol-2-yl)phenyl]carbonyl}piperidin-3-yl]oxy}pyridine-4-carboxylate;
dimethyl 2-{[(3R,6R)-6-methyl-1-{[2-(2H-1,2,3-triazol-2-yl)phenyl]carbonyl}piperidin-3-yl]oxy}pyridine-3,4-dicarboxylate;
methyl 2-methyl-6-{[(3R,6R)-6-methyl-1-{[2-(2H-1,2,3-triazol-2-yl)phenyl]carbonyl}piperidin-3-yl]oxy}pyridine-4-carboxylate;
methyl 3-fluoro-2-{[(3R,6R)-6-methyl-1-{[2-(2H-1,2,3-triazol-2-yl)phenyl]carbonyl}piperidin-3-yl]oxy}pyridine-4-carboxylate;
methyl 2-{[(3R,6R)-1-{[6-methoxy-2-(2H-1,2,3-triazol-2-yl)pyridin-3-yl]carbonyl}-6-methylpiperidin-3-yl]oxy}pyridine-4-carboxylate;
methyl 5-methoxy-2-{[(3R,6R)-6-methyl-1-{[2-(2H-1,2,3-triazol-2-yl)phenyl]carbonyl}piperidin-3-yl]oxy}pyridine-4-carboxylate;
methyl 5-methyl-2-{[(3R,6R)-6-methyl-1-{[2-(2H-1,2,3-triazol-2-yl)phenyl]carbonyl}piperidin-3-yl]oxy}pyridine-4-carboxylate;
methyl 2-({(3R,6R)-1-[(6-methoxy-2-pyrimidin-2-ylpyridin-3-yl)carbonyl]-6-methylpiperidin-3-yl}oxy)pyridine-4-carboxylate;
and pharmaceutically acceptable salts thereof.

In some embodiments, the OX1R antagonist of the present invention is selected from tertiary amide orexin receptor antagonists that are disclosed in WO 2011053522 A1. In some embodiments, the OX1R antagonist of the present invention are selected from the group consisting of:
N-[2-(5,6-dimethoxy-3 pyridinyl)ethyl]-N-[3-(4-methoxyphenyl)-1-methylpropyl]-6-methyl-2-pyridinecarboxamide;
6-chloro-N-[2-(5,6-dimethoxypyridinecarboxamide;
N-f2-(5,6-dimethoxy-2-pyridinyl)ethyl]-6-methyl-N-(1-methyl-3-phenylpropyl)-2-pyridinecarboxamide;
N-[2-(5,6-dimethoxypyridin-2-yl)ethyl]-6-(dimethylamino)-N-[4-(4-methoxyphenyl)butan-2-yl]pyridine-2-carboxamide;
6-chloro-N-[2-(5,6-dimethoxypyridin-2-yl)ethyl]-N-(4-phenylbutan-2-yl)pyridine-2-carboxamide
N-[2-(5,6-dimethoxypyridin-2-yl)ethyl]-3-methyl-N-(4-phenylbutan-2-yl)benzamide;
6-bromo-N-[2-(5,6-dimethoxypyridin-2-yl)ethyl]-N-(4-phenylbutan-2-yl)pyridine-2-carboxamide;
N-[2-(5,6-dimethoxypyridin-2-yl)ethyl]-6-fluoro-N-(4-phenylbutan-2-yl)pyridine-2-carboxamide;
N-[2-(5,6-dimethoxypyridin-2-yl)ethyl]-N-(4-phenylbutan-2-yl)-6-(propan-2-yl)pyridine-2-carboxamide;
6-cyano-N-[2-(5,6-dimethoxypyridin-2-yl)ethyl]-N-(4-phenylbutan-2-yl)pyridine-2-carboxamide
6-cyclopropyl-N-[2-(5,6-dimethoxypyridin-2-yl)ethyl]-N-(4-phenylbutan-2-yl)pyridine-2-carboxamide;
N-[2-(5,6-dimethoxypyridin-2-yl)ethyl]-6-ethyl-N-(4-phenylbutan-2-yl)pyridine-2-carboxamide
N-[2-(5,6-dimethoxypyridin-2-yl)ethyl]-6-methylcarboxamide;
6-chloro-N-[2-(5,6-dimethoxypyridin-2-yl)methylcarboxamide;
and pharmaceutically acceptable salts thereof, In some embodiments, the OX1R antagonist of the present invention is selected from 3-ester-4-substituted orexin receptor antagonists that are disclosed in WO 2014099697 A1. In some embodiments, the OX1R antagonist of the present invention is selected from the group consisting of:
ethyl 4-methyl-2-{[(3R,6R)-6-methyl-1-{[2-(2H-1,2,3-triazol-2-yl)phenyl]carbonyl}piperidin-3-yl]oxy}pyridine-3-carboxylate;
methyl 4-methyl-2-{[(3R,6R)-6-methyl-1-{[2-(2H-1,2,3-triazol-2-yl)phenyl]carbonyl}piperidin 3-yl]oxy}pyridine-3-carboxylate;
methyl 4-(methylsulfanyl)-2-{[(3R,6R)-6-methyl-1-{[2-(2H-1,2,3-triazol-2-yl)phenyl]carbonyl}piperidin-3-yl]oxy}pyridine-3-carboxylate;
methyl 2-({(3R,6R)-6-methyl-1-[(2-pyrimidin-2-ylphenyl)carbonyl]piperidin-3-yl}oxy)-4-(methylsulfanyl)pyridine-3-carboxylate;
methyl 2-({(3R,6R)-1-[(5-fluoro-2-pyrimidin-2-ylphenyl)carbonyl]-6-methylpiperidin-3-yl}oxy)-4-(methylsulfanyl)pyridine-3-carboxylate;
methyl 2-({(3R,6R)-1-[(4-fluoro-2-pyrimidin-2-ylphenyl)carbonyl]-6-methylpiperidin-3-yl}oxy)-4-(methylsulfanyl)pyridine-3-carboxylate;
methyl 2-({(3R,6R)-1-[(3-fluoro-2-pyrimidin-2-ylphenyl)carbonyl]-6-methylpiperidin-3-yl}oxy)-4-(methylsulfanyl)pyridine-3-carboxylate;
methyl 4-azetidin-1-yl-2-{[(3R,6R)-6-methyl-1-{[2-(2H-1,2,3-triazol-2-yl)phenyl]carbonyl}piperidin-3-yl]oxy}pyridine-3-carboxylate;
methyl 4-(4-methylpiperazin-1-yl)-2-{[(3R,6R)-6-methyl-1-{[2-(2H-1,2,3-triazol-2-yl)phenyl]carbonyl}-piperidin-3-yl]oxy}pyridine-3-carboxylate;
methyl 4-ethyl-2-{[(3R,6R)-6-methyl-1-{[2-(2H-1,2,3-triazol-2-yl)phenyl]carbonyl}piperidin-3 yl]oxy}pyridine-3-carboxylate;
methyl 4-tert-butyl-2-{[(3R,6R)-6-methyl-1-{[2-(2H-1,2,3-triazol-2-yl)phenyl]carbonyl}piperidin-3-yl]oxy}pyridine-3-carboxylate;
methyl 4-(1-methylethyl)-2-{[(3R,6R)-6-methyl-1-{[2-(2H-1,2,3-triazol-2-yl)phenyl]carbonyl}piperidin-3-yl]oxy}pyridine-3-carboxylate;
methyl 4-cyclopropyl-2-{[(3R,6R)-6-methyl-1-{[2-(2H-1,2,3-triazol-2-yl)phenyl]carbonyl}piperidin-3-yl]oxy}pyridine-3-carboxylate;
methyl 4-cyclobutyl-2-{[(3R,6R)-6-methyl-1-{[2-(2H-1,2,3-triazol-2-yl)phenyl]carbonyl}piperidin-3-yl]oxy}pyridine-3-carboxylate;

methyl 2-methyl-6-{[(3R,6R)-6-methyl-1-{[2-(2H-1,2,3-triazol-2-yl)phenyl]carbonyl}piperidin 3-yl]oxy}benzoate;

methyl 2-(1-methylethyl)-6-{[(3R,6R)-6-methyl-1-{[2-(2H-1,2,3-triazol-2-yl)phenyl]carbonyl}piperidin-3-yl]oxy}benzoate; and ethyl 4-ethyl-2-{[(3R,6R)-6-methyl-1-{[2-(2H-1,2,3-triazol-2-yl)phenyl]carbonyl}piperidin-3-yl]oxy}pyridine-3-carboxylate;

and pharmaceutically acceptable salts thereof.

In some embodiments, the OX1R antagonist of the present invention is selected from the group consisting of 2,5-disubstituted thiomorpholine orexin receptor antagonists that are disclosed in WO 2013059163 A1. In some embodiments, the OX1R antagonist of the present invention is selected from the group consisting of:

[(2R,5R)-2-{[(5-fluoropyridin-2-yl)oxy]methyl}-5-methylthio morpholin-4-yl][5-methyl-2-(2H-1,2,3-triazol-2-yl)phenyl]methanone;

(2R,5R)-5-methyl-2-[(pyridin-2-yloxy)methyl]-4-{[2-(2H-1,2,3-triazol-2-yl)phenyl]carbonyl}thiomorpholine;

(2R,5R)-2-{[(5-fluoropyridin-2-yl)oxy]methyl}-5-methyl-4-{[2-(2H-1,2,3-triazol-2-yl)phenyl]carbonyl}thiomorpholine;

(2R,5R)-5-methyl-2-{[(5-methylpyridin-2-yl)oxy]methyl}-4-{[2-(2H-1,2,3-triazol-2-yl)phenyl]carbonyl}thiomorpholine;

(2R,5R)-2-{[(5-chloropyridin-2-yl)oxy]methyl}-5-methyl-4-{[2-(2H-1,2,3-triazol-2-yl)phenyl]carbonyl}thiomorpholine;

6-{[(2R,5R)-5-methyl-4-{[2-(2H-1,2,3-triazol-2-yl)phenyl]carbonyl}thiomorpholin-2-yl]methoxy}pyridine-3-carbonitrile;

(2R,5R)-5-methyl-4-{[2-(2H-1,2,3-triazol-2-yl)phenyl]carbonyl}-2-({[5-(trifluoromethyl)pyridin-2-yl]oxy}methyl)thiomorpholine;

(2R,5R)-2-{[(3-chloropyridin-2-yl)oxy]methyl}-5-methyl-4-{[2-(2H-1,2,3-triazol-2-yl)phenyl]carbonyl}thiomorpholine;

2-{[(2R,5R)-5-methyl-4-{[2-(2H-1,2,3-triazol-2-yl)phenyl]carbonyl}thiomorpholin-2-yl]methoxy}pyridine-3-carbonitrile;

(2R,5R)-5-methyl-2-{[(4-methylpyridin-2-yl)oxy]methyl}-4-{[2-(2H-1,2,3-triazol-2-yl)phenyl]carbonyl}thiomorpholine;

(2R,5R)-5-methyl-2-[(pyrimidin-2-yloxy)methyl]-4-{[2-(2H-1,2,3-triazol-2-yl)phenyl]carbonyl}thiomorpholine;

(2R,5R)-2-{[(5-chloro-4-methylpyrimidin-2-yl)oxy]methyl}-5-methyl-4-{[2-(2H-1,2,3-triazol-2-yl)phenyl]carbonyl}thiomorpholine;

(2R,5R)-2-{[(4-chloro-5-methylpyrimidin-2-yl)oxy]methyl}-5-methyl-4-{[2-(2H,2,3-M yl)phenyl]carbonyl}thiomorpholine;

(2R,5R)-2-{[(4-chloro-5-methoxypyrimidin-2-yl)oxy]methyl}-5-methyl-4-{[2-(2H-1,22-yl)phenyl]carbonyl}thiomorpholine;

[(2R,5R)-2-{[(5-fluoropyridin-2-yl)oxy]methyl}-5-methyl-1-oxidothiomorpholin-4-1,2,3-triazol-2-yl)phenyl]methanone;

[(2R,5R)-2-{[(5-fluoropyridin-2-yl)oxy]methyl}-5-m(2H-1,2,3-triazol-2-yl)phenyl]methanone; and {(2R,5R)-5-methyl-2-[(pyridine-2-ylsulfanyl)methyl]thiomorpholin-4-yl}[2-(2H-1,2,3-triazol-2-yl)phenyl]methanone;

and pharmaceutically acceptable salt thereof.

In some embodiments, the OX1R antagonist of the present invention is selected from piperidinyl alkyne orexin receptor antagonists that are disclosed in WO 2013062857 A1. In some embodiments, the OX1R antagonist of the present invention is selected from the group consisting of:

[(2R,5R)-2-memyl-5-(yridin-2-ylemynyl)piperidin-1-yl][2-(2H-1,2,3-triyl)phenyl]methanone;

2-{[(3 S,6R)-6-methyl-1-{[2-(2H-1,2,3-triazol-2-yl)phenyl]carbonyl}piperidin-3-yl]ethynyl}pyridine;

4-{[(3 S,6R)-6-memyl-1-{[2-(2H,2₅ 3-tria2ol-2-yl)phenyl]carbonyl}piperidin-3-yl]ethynyl}pyridine;

3-{[(3 S,6R)-6-methyl-1-{[2-(2H-1,2,3-triazol-2-yl)phenyl]carbonyl}piperidin-3-yl]ethynyl}pyridine;

3-{[(3 S,6R)-6-methyl-1-{[2-(2H-1,2,3-triazol-2-yl)phenyl]carbonyl}piperidin-3-yl]ethynyl}pyridin-2-ol;

3-{[(3S,6R)-6-methyl-1-{[2-(2H-1,2,3-triazol-2-yl)phenyl]carbonyl}piperidin-3-yl]ethynyl}pyridin-4-ol;

(5-{[(3 S,6R)-6-merayl-1-{[2-(2H-1,2,3-triayl]ethynyl}pyridin-2-yl)methanol;

(6-{[(3 S,6R)-6-methyl-1-{[2-(2H-1,2,3-triazol-2-yl)phenyl]carbonyl}piperidin-3-yl]ethynyl}pyridin-3-yl)methanol;

(6-{[(3 S,6R)-6-methyl-1-{[2-(2H-1,2,3-triazol-2-yl)phenyl]carbonyl}piperidin-3-yl]ethynyl}pyridin-2-yl)methanol;

(2-{[(3 S,6R)-6-memyl-1-{[2-(2H,2,3-triazol-2-yl)phenyl]carbonyl}piperidin-3-yl]ethynyl}pyridin-4-yl)methanol;

(4-{[(3 S,6R)-6-methyl-1-{[2-(2H-1,2J3-triazol-2-yl)phenyl]carbonyl}piperidin-4-yl]ethynyl}pyridin-2-yl)methanol;

{(2R,5S)-5-[(5-fluoropyridin-2-yl)ethynyl]-2-methylpiperidin-1-yl}[5-methyl-2-(2H-1,2,3-triazol-2-yl)phenyl]methanone;

[5-methyl-2-(2H-1,2,3-azol-2-yl)phenyl][2-(phenyle1hynyl)piperidin-1-yl 1-{[5-methyl-2-(2H-1,2,3-triazol-2-yl)phenyl]carbonyl}-2-(phenylethynyl)piperidine;

5-fluoro-2-[(1-{[5-methyl-2-(2H-1,2,3-triazol-2-yl)phenyl]carbonyl}piperidin-2-yl)ethynyl]pyridine;

2-[(4-fluorophenyl)ethynyl]-1-{[5-methyl-2-(2H-1,2,3-1xiazol-2-yl)phenyl]2-[(1-{[5-methyl-2-(2H-1,2,3-triazol-2-yl)phenyl]carbonyl}piperidin-2-yl)ethynyl]quinoline;

1-{[5-methyl-2-(2H-1,2,3-triazol-2-yl)phenyl]carbonyl}-2-(naphthalen-2-ylethynyl)piperidine;

(2-merayl-5-phenyl-1,3-thiazol-4-yl) [2-(phenylethynyl)piperidin-1-yl]methanone;

1-[(2-methyl-5-phenyl-1,3-thiazol-4-yl)carbonyl]-2-(phenylethynyl)piperidine;

and pharmaceutically acceptable salts thereof.

In some embodiments, the OX1R antagonist of the present invention is selected from 2-pyridyloxy-3-nitrile-4-substituted orexin receptor antagonists that are disclosed in WO 2014099698 A1. In some embodiments, the OX1R antagonist of the present invention is selected from the group consisting of:

4-(Methylsulfanyl)-2-{[(3R,6R)-6-methyl-1-{[2-(2H-1,2,3-triazol-2-yl)phenyl]carbonyl}-piperidin-3-yl]oxy}pyridine-3-carbonitrile;

4-Methyl-2-{[(3R,6R)-6-methyl-1-{[2-(2H-1,2,3-triazol-2-yl)phenyl]carbonyl}piperidin-3-yl]oxy}pyridine-3-carbonitrile;

2-{[(3R,6R)-1-{[4-Chloro-2-(2H-1,2,3-triazol-2-yl)phenyl]carbonyl}-6-methylpiperidin-3-yl]oxy}-4-methylpyridine-3-carbonitrile;

4-methyl-2-{[(3R,6R)-6-methyl-1-{[4-(2H-1,2,3-triazol-2-yl)pyridin-3-yl]carbonyl}piperidin-3 yl]oxy}pyridine-3-carbonitrile;

2-{[(3R,6R)-1-{[2-fluoro-6-(2H-1,2,3-triazol-2-yl)phenyl]carbonyl}-6-methylpiperidin-3-yl]oxy}-4-methylpyridine-3-carbonitrile;

2-{[(3R,6R)-1-{[2-methoxy-6-(2H-1,2,3-triazol-2-yl)phenyl]carbonyl}-6-methylpiperidin-3-yl]oxy}-4-methylpyridine-3-carbonitrile;

4-methyl-2-{[(3R,6R)-6-methyl-1-{[3-methyl-2-(2H-1,2,3-triazol-2-yl)phenyl]carbonyl}piperidin-3-yl]oxy}pyridine-3-carbonitrile;

2-{[(3R,6R)-1-{[4-fluoro-2-(2H-1,2,3-triazol-2-yl)phenyl]carbonyl}-6-methylpiperidin-3-yl]oxy}-4-methylpyridine-3-carbonitrile;

2-{[(3R,6R)-1-{[4-methoxy-2-(2H-1,2,3-triazol-2-yl)phenyl]carbonyl}-6-methylpiperidin-3-yl]oxy}-4-methylpyridine-3-carbonitrile;

2-{[(3R,6R)-1-{[3-fluoro-2-(2H-1,2,3-triazol-2-yl)phenyl]carbonyl}-6-methylpiperidin-3-yl]oxy}-4-methylpyridine-3-carbonitrile;

4-methyl-2-{[(3R,6R)-6-methyl-1-{[5-methyl-2-(2H-1,2,3-triazol-2-yl)phenyl]carbonyl}piperidin-3-yl]oxy}pyridine-3-carbonitrile;

2-{[(3R,6R)-1-{[6-methoxy-2-(2H-1,2,3-triazol-2-yl)pyridin-3-yl]carbonyl}-6-methylpiperidin-3-yl]oxy}-4-methylpyridine-3-carbonitrile;

and pharmaceutically acceptable salts thereof.

By a "therapeutically effective amount" is meant a sufficient amount of OX1R antagonist of the present invention to treat cancer at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the OX1R antagonist of the present invention is administered in combination with a chemotherapeutic agent. The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycin, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; amino levulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylamine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the OX1R antagonist of the present invention is administered in combination with a targeted cancer therapy. Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the OX1R antagonist of the present invention is administered in combination with an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ). Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents. Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants. A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include Proleukin® (IL-2; Chiron Corporation) and Neumega®

(IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin). In addition to having specific or non-specific targets, immunotherapeutic agents can be active, i.e. stimulate the body's own immune response, or they can be passive, i.e. comprise immune system components that were generated external to the body. Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins. Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22. Other examples include anti-CTLA4 antibodies (e.g. Ipilimumab), anti-PD1 antibodies, anti-PDL1 antibodies, anti-TIMP3 antibodies, anti-LAG3 antibodies, anti-B7H3 antibodies, anti-B7H4 antibodies or anti-B7H6 antibodies. In some embodiments, antibodies include B cell depleting antibodies. Typical B cell depleting antibodies include but are not limited to anti-CD20 monoclonal antibodies [e.g. Rituximab (Roche), Ibritumomab tiuxetan (Bayer Schering), Tositumomab (GlaxoSmithKline), AME-133v (Applied Molecular Evolution), Ocrelizumab (Roche), Ofatumumab (HuMax-CD20, Gemnab), TRU-015 (Trubion) and IMMU-106 (Immunomedics)], an anti-CD22 antibody [e.g. Epratuzumab, Leonard et al., Clinical Cancer Research (Z004) 10: 53Z7-5334], anti-CD79a antibodies, anti-CD27 antibodies, or anti-CD19 antibodies (e.g. U.S. Pat. No. 7,109,304), anti-BAFF-R antibodies (e.g. Belimumab, GlaxoSmithKline), anti-APRIL antibodies (e.g. anti-human APRIL antibody, ProSci inc.), and anti-IL-6 antibodies [e.g. previously described by De Benedetti et al., J Immunol (2001) 166: 4334-4340 and by Suzuki et al., Europ J of Immunol (1992) 22 (8) 1989-1993, fully incorporated herein by reference]. The immunotherapeutic treatment may also consist of allografting, in particular, allograft with hematopoietic stem cell HSC. The immunotherapeutic treatment may also consist in an adoptive immunotherapy as described by Nicholas P. Restifo, Mark E. Dudley and Steven A. Rosenberg "Adoptive immunotherapy for cancer: harnessing the T cell response, Nature Reviews Immunology, Volume 12, April 2012). In adoptive immunotherapy, the subject's circulating lymphocytes, NK cells, are isolated amplified in vitro and readministered to the subject. The activated lymphocytes or NK cells are most preferably be the subject's own cells that were earlier isolated from a blood or tumor sample and activated (or "expanded") in vitro.

In some embodiments, the OX1R antagonist of the present invention is administered in combination with a radiotherapeutic agent. The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

According to the invention, the OX1R antagonist of the present invention is administered to the subject in the form of a pharmaceutical composition. Typically, the OX1R antagonist of the present invention may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The OX1R antagonist of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

A further object of the invention relates to a method for treating a cancer in a subject in thereof comprising the steps consisting of i) determining the expression level of OX1R in a tumour tissue sample obtained from the subject, ii) comparing the expression level determined at step i) with a reference value and iii) administering the subject with a therapeutically effective amount of an OX1R antagonist when the level determined at step i) is higher than the reference value.

The expression level of OX1R may be determined by any well known method in the art. For example methods for determining the quantity of mRNA are well known in the art. Typically the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous. Alternatively an immunohistochemistry (IHC) method may be used. IHC specifically provides a method of detecting targets in a sample or tissue specimen in situ. The overall cellular integrity of the sample is maintained in IHC, thus allowing detection of both the presence and location of the targets of interest (i.e. OX1R). Typically a sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan). In particular embodiment, a tumor tissue section may be mounted on a slide or other support after incubation with antibodies directed against OX1R. Then, microscopic inspections in the sample mounted on a suitable solid support may be performed. For the production of photomicrographs, sections comprising samples may be mounted on a glass slide or other planar support, to highlight by selective staining the presence of the proteins of interest.

A "reference value" can be a "threshold value" or a "cut-off value". Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Typically, the threshold value is derived from the OX1R expression level (or ratio, or score) determined in a tumor tissue sample derived from one or more subjects having sufficient amount of OX1R level to get an efficient treatment with the OX1R agonist. Furthermore, retrospective measurement of the OX1R expression levels (or ratio, or scores) in properly banked historical subject samples may be used in establishing these threshold values.

The invention will be further illustrated by the following figures and examples. However, these examples and figures should not be interpreted in any way as limiting the scope of the present invention.

FIGURES

FIG. 1: Effect of orexin-A and SB408124 antagonist on Ca2+ mobilization in HEK-OX1R cells. Top, HEK-OX1R cells were incubated with fluorescence probe (FluoForte) for 45 min. at 37° C. according to FluoForte calcium assay kit (Enzo Life Sciences). 1 µM of OxA was added to cells and fluorescence emission was measured on TECAN Infinite 200 fluorospectrophotometer. Bottom, HEK-OX1R cells were incubated with fluorescence probe (FluoForte) for 45 min. at 37° C. and then incubated with 1 µM of SB408124 for 1 h at 37° C. After pre-incubation, 1 µM of OxA was added to cells and fluorescence emission was measured.

Figure 2:
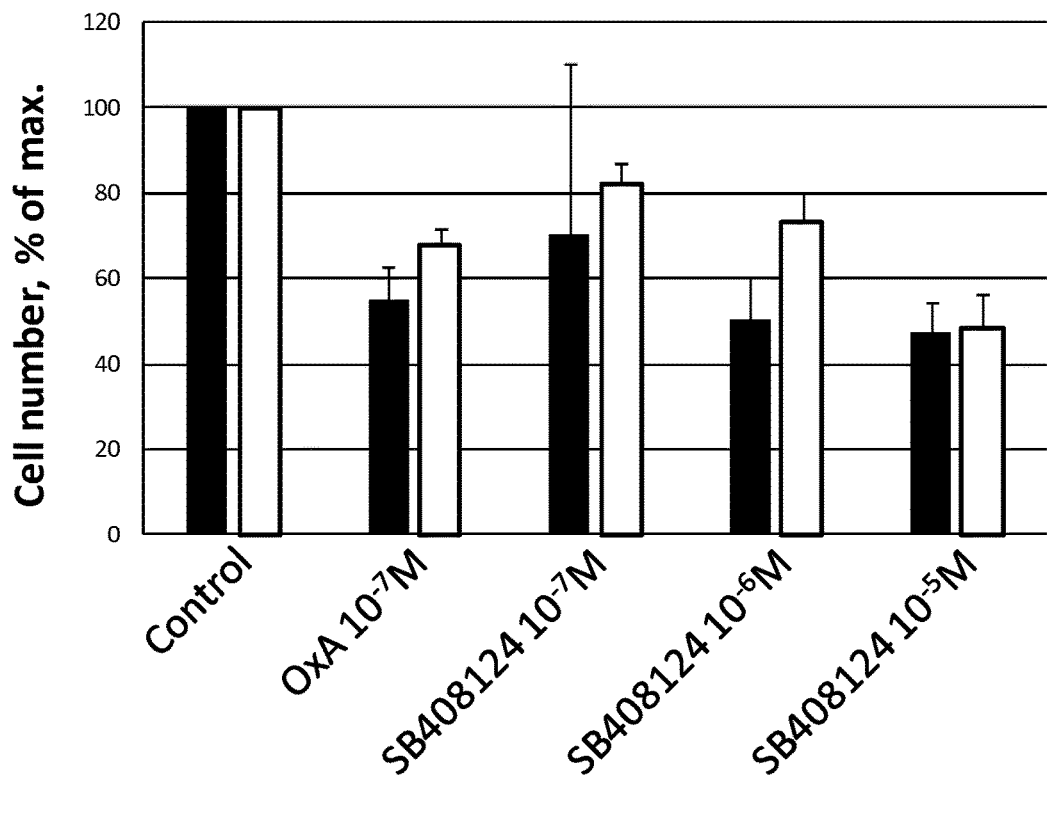

FIG. 2: Determination of the inhibition of cellular growth of HEK-OX1R cells and colon adenocarcinoma cells (HT-29) induced by 0.104 of OxA or various concentrations of SB408124 antagonist. HEK-OX1R cells (black column) and HT-29 cells (white column) were incubated with 0.1 µM of OxA and indicated increasing concentration of SB408124, and cells were counted after 48 hr incubation. Results are expressed as the percentage of total viable cells.

Figure 3:
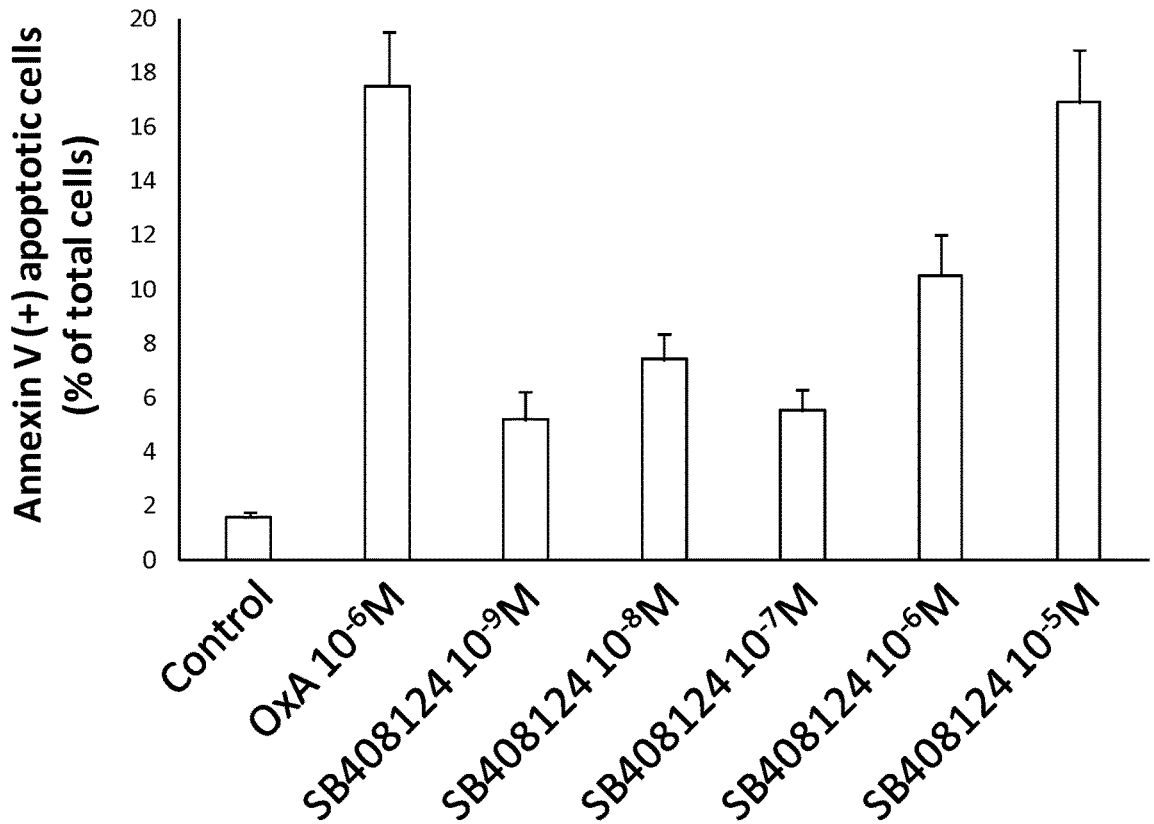

FIG. 3: Effect of orexin-A and SB408124 antagonist on apoptosis in OX1R expressing colon adenocarcinoma cells, HT-29. HT-29 cells were challenged with 1 µM orexin-A or various concentration of SB408124 for 48 h. Apoptosis was measured by determination of annexin V-PE binding, and results are expressed as the percentage of apoptotic cells. Results are means±SE of three experiments. ***P<0.001.

Figure 4:
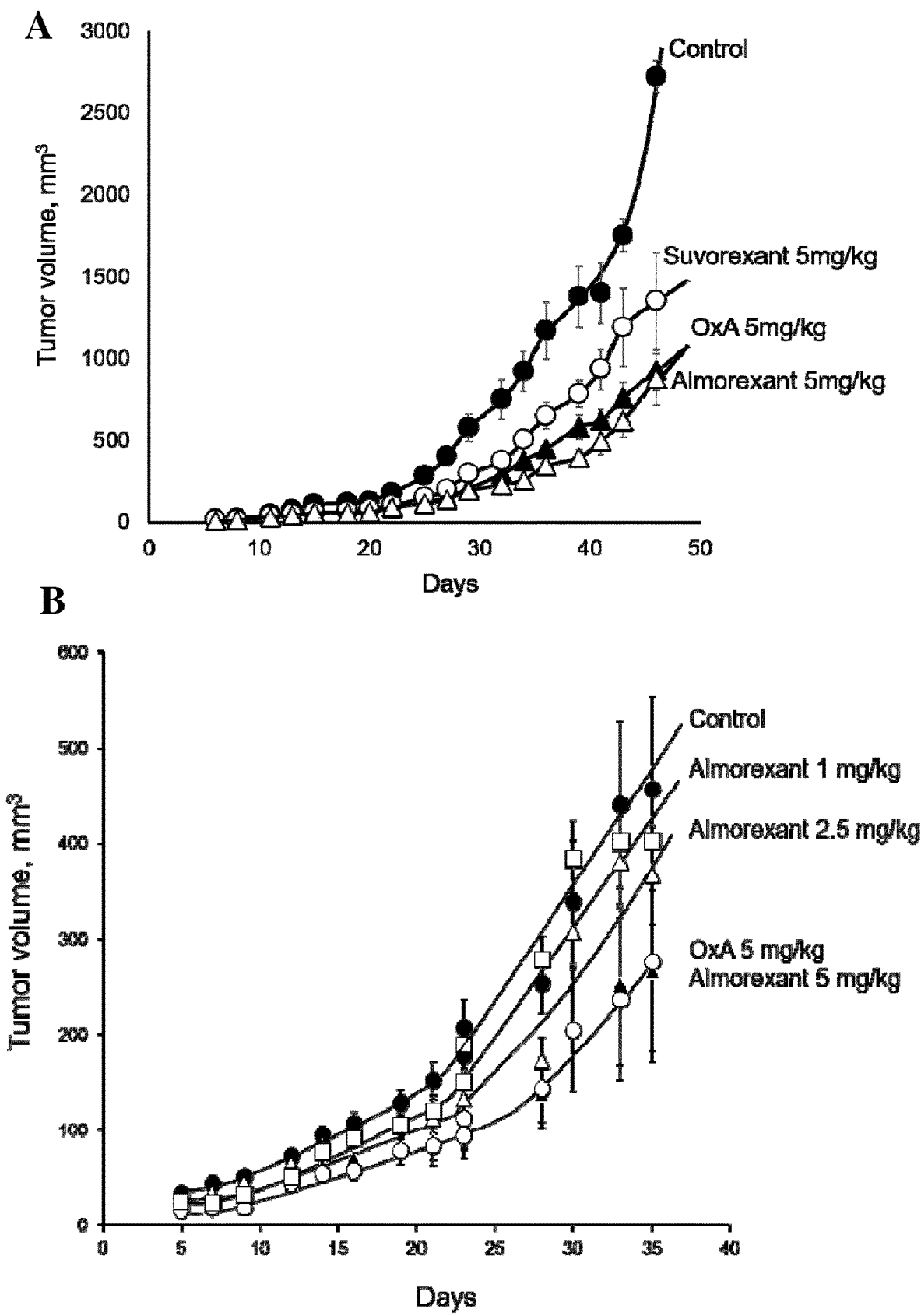

FIG. 4: Effect of ip inoculation of OxA (▲), Suvorexant (○) and Almorexant (Δ) on the growth of tumors developed by xenografting human colon cancer cells in nude mice. A. LoVo cells were inoculated in the flank of nude mice at day 0. Mice were injected 2 times/week intraperitoneally with 100 µg of OxA, Suvorexant or Almorexant in 100 µl solutions or with 100 µl of PBS (●) for controls. After 48 days of treatment, mice were sacrificed and tumor volume and weight were then recorded. The development of tumors was followed by caliper measurement. B. treatment (2 injections/week) with various doses of Almorexant (1 mg/kg (□), 2.5 mg/kg (Δ) or 5 mg/kg (○)) compared to OxA treatment (5 mg/kg, ▲). Control was performed by injection of 100 µl PBS (●).

EXAMPLE

Example 1

Material & Methods
Ca2+ Mobilization Assay:

HEK cells expressing recombinant native OX1R (HEK-OX1R) cells were seeded in 96-wells plate, grown and maintained at 37° C. in a humidified 5% $CO_2$/air incubator. 80,000 cells/well were incubated with FluoForte probe according to FluoForte calcium assay kit (ENZO life Sciences, Farmingdale, N.Y., USA) for 45 min. at 37° C. and then incubated with or without 1 µM of SB408124 antagonist for 1 h at 37° C. After pre-incubation, 1 µM of OxA was added and fluorescence was determined using TECAN Infinite 200 fluorospectrophotometer.

Cells Growth Determination and Apoptosis Assay:

HEK-OX1R cells or colon adenocarcinoma HT-29 cells were seeded, grown and maintained at 37° C. in a humidified 5% $CO_2$/air incubator. After 24 hr culture, cells were treated with or without Orexin-A peptide or SB408124 antagonist, previously dissolved in DMSO, to be tested at the concentration indicated in the figure legends. After 48 hr of treatment, adherent cells were harvested by TriplE (Life Technologies, Saint Aubin, France) and manually counted. Apoptosis was determined using the Guava PCA system and the Guava nexin kit.

Results

As shown in FIG. 1, OxA induced a large and transient $Ca^{2+}$ mobilization in HEK-OX1R cells. In contrast, the preincubation of cells with 1 µM of SB408124 antagonist totally abolished the induced-$Ca^{2+}$ mobilization (FIG. 1) confirming the antagonist effect of SB408124 on intracellular calcium release mediated by OX1R trough Gq and phospholipase C pathway. In the second phase, we determined the antagonist or agonist effect of SB408124 on cellular growth and apoptosis of HEK-OX1R cells and colon cancer cell line, HT-29 As shown in FIG. 2, OxA induced a strong inhibition of cellular growth of HEK-OX1R and HT-29 cells. Surprisingly, SB408124 antagonist induced also a strong inhibition in a dose-dependent manner of cellular growth of HEK-OX1R and HT-29 cells. As previously shown, orexins were able to trigger an inhibition of cellular growth by induction of mitochondrial apoptosis. As expected, OxA induced an apoptotic effect in HT-29 cells (FIG. 3). Likewise, SB408124 antagonist was also able to induce in a dose-dependent manner cell apoptosis in HT-29 cells. Taken together these results demonstrated that SB408124 was a full antagonist for OX1R-mediated calcium mobilization but a full agonist for OX1R-mediated mitochondrial apoptosis in colon cancer cell line.

Example 2

The inventors investigated the effect of intraperitoneal inoculation of OxA, Suvorexant and Almorexant on the growth of tumors developed by xenografting human colon cancer cells (LoVo cells) in nude mice. As shown in FIG. 4A, nude mice bearing human colon cancer xenografts treated with OX1R antagonists Suvorexant and Almorexant similarly to mice treated with OxA developed significantly smaller tumors that control mice treated with PBS. Accordingly, the inventors demonstrated that OX1R antagonists and OxA inhibit tumor growth. Likewise, OX1R antagonist Almorexant was also able to induce in a dose-dependent manner tumor growth inhibition (FIG. 4B).

REFERENCES

Throughout this application, various references describe the state of the art to which this invention pertains. The disclosures of these references are hereby incorporated by reference into the present disclosure.

The invention claimed is:
1. A method of treating a colorectal cancer in a subject in need thereof, wherein cells of said cancer express orexin-1-receptor (OX1R), comprising administering to the subject a therapeutically effective amount of at least one OX1R antagonist to treat said colorectal cancer, wherein the OX1R antagonist is selected from the group consisting of SB408124, Suvorexant and Almorexant, and wherein said cells of said colorectal cancer expressing said OX1R.
2. The method of claim 1 wherein the OX1R antagonist is administered in combination with a chemotherapeutic agent.
3. The method of claim 2 wherein the chemotherapeutic agent is selected from the group consisting of alkylating agents; alkyl sulfonates; aziridines; ethylenimines and/or methylamelamines; acetogenins; a camptothecin; bryostatin; callystatin; CC-1065; cryptophycins; dolastatin; duocarmycin; eleutherobin; pancratistatin; a sarcodictyin; spongistatin; nitrogen mustards; nitrosureas; antibiotics; anti-metabolites; folic acid analogues; purine analogs; pyrimidine analogs; androgens; anti-adrenals; folic acid replenisher; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes; urethan; vindesine; dacarbazine; mannomustine; mitobromtol; mitolactol; pipobroman; gacytosine; arabinoside; cyclophosphamide; thiotepa; taxoids; chlorambucil; gemcitabine; 6-thioguanine; mercaptopurine; methotrexate; platinum analogs; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above.

4. The method of claim 1 wherein the OX1R antagonist is administered in combination with a tyrosine kinase inhibitor selected from the group consisting of dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), and MK-2206 (8-[4-aminocyclobutyl)phenyl]-9-phenyl-1,2,4-triazolo[3,4-f][1,6]naphthyridin-3(2H)-one hydrochloride).

5. The method of claim 1 wherein the OX1R antagonist is administered in combination with an immunotherapeutic agent.

6. The method of claim 5 wherein immunotherapeutic agent is an antibody selected from the group consisting of rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), BL22 an anti-CTLA4 antibody, an anti-PD1 antibody, an anti-PDL1 antibody, an anti-TIMP3 antibody, an anti-LAG3 antibody, an anti-B7H3 antibody, an anti-B7H4 antibody or an anti-B7H6 antibody.

7. The method of claim 1 wherein the OX antagonist is administered in combination with a radiotherapeutic agent.

8. The method of claim 3, wherein the chemotherapeutic agent is an anti-estrogen or an anti-androgen.

9. The method of claim 3, wherein the anti-estrogen is tamoxifen, raloxifene, an aromatase inhibiting 4(5)-imidazole, 4-hydroxytamoxifen, trioxifene, keoxifene, LY117018, onapristone or toremifene (Fareston).

10. The method of claim 3, wherein the anti-androgen is flutamide, nilutamide, bicalutamide, leuprolide or goserelin.

11. The method of claim 3, wherein
the alkylating agent is thiotepa or cyclosphosphamide;
the alkyl sulfonate is busulfan, improsulfan or piposulfan;
the aziridine is benzodopa, carboquone, meturedopa, or uredopa;
the ethylenimines and/or methylamelamines is altretamine, triethylenemelamine, trietylenephosphoramide, triethylenethiophosphaorarnide or trimethylolomelamine;
the nitrogen mustads is chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide or uracil mustard;
the nitrosurea is carmustine, chlorozotocin, fotemustine, lomustine, nimustine or ranimustine;
the antibiotic is selected from the group consisting of enediyne antibiotic, an aclacinomysin, actinomycin, authramycin, azaserine, a bleomycin, cactinomycin, carabicin, canninomycin, carzinophilin, a chromomycin, dactinomycin, daunorubicin, detorubicin, 6-diazo-5-oxo-L-norleucine, doxorubicin, epirubicin, esorubicin, idanrbicin, marcellomycin, a mitomycin, mycophenolic acid, nogalarnycin, an olivomycin, peplomycin, potfiromycin, puromycin, quelamycin, rodorubicin, streptomgrin, streptozocin, tubercidin, ubenimex, zinostatin and zorubicin;
the anti-metabolite is methotrexate or 5-fluorouracil (5-FU);
the folic acid analogue is denopterin, methotrexate, pteropterin or trimetrexate;
the purine analog is fludarabine, 6-mercaptopurine, thiamiprine or thioguanine;
the pyrimidine analog is selected from the group consisting of ancitabine, azacitidine, 6-azauridine, carmofur, cytarabine, dideoxyuridine, doxifluridine, enocitabine, floxuridine and 5-FU;
the androgen is calusterone, dromostanolone propionate, epitiostanol, mepitiostane or testolactone;
the anti-adrenal is aminoglutethimide, mitotane or trilostane;
the folic acid replenisher is frolinic acid;
the maytansinoid is maytansine or an ansamitocin; and
the platinum analog is cisplatin or carboplatin.

* * * * *